(12) United States Patent
Ebata et al.

(10) Patent No.: US 8,440,384 B2
(45) Date of Patent: May 14, 2013

(54) COMPOUND, SALT, AND RADIATION-SENSITIVE RESIN COMPOSITION

(75) Inventors: Takuma Ebata, Tokyo (JP); Tomoki Nagai, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 12/760,509

(22) Filed: Apr. 14, 2010

(65) Prior Publication Data

US 2010/0221659 A1     Sep. 2, 2010

Related U.S. Application Data

(63) Continuation of application No. PCT/JP2008/068533, filed on Oct. 14, 2008.

(30) Foreign Application Priority Data

Oct. 15, 2007  (JP) ................... 2007-267700

(51) Int. Cl.
    *G03F 7/039*   (2006.01)
(52) U.S. Cl.
    USPC ........ 430/270.1; 430/326; 430/905; 430/910; 430/921; 430/925
(58) Field of Classification Search .......... None
    See application file for complete search history.

(56) References Cited

U.S. PATENT DOCUMENTS

| | | |
|---|---|---|
| 2003/0113658 A1 | 6/2003 | Ebata et al. |
| 2003/0170561 A1* | 9/2003 | Iwasawa et al. ........... 430/270.1 |
| 2005/0186505 A1* | 8/2005 | Kodama et al. ........... 430/270.1 |
| 2006/0194982 A1 | 8/2006 | Harada et al. |
| 2006/0228648 A1 | 10/2006 | Ohsawa et al. |
| 2007/0042290 A1* | 2/2007 | Inabe et al. ................ 430/270.1 |
| 2007/0054214 A1 | 3/2007 | Ebata et al. |
| 2007/0065752 A1 | 3/2007 | Yamamoto et al. |
| 2007/0122750 A1 | 5/2007 | Yamaguchi et al. |

FOREIGN PATENT DOCUMENTS

| | | |
|---|---|---|
| JP | 2-27660 | 1/1990 |
| JP | 2004-2252 | 1/2004 |
| JP | 2005-148291 | 6/2005 |
| JP | 2006-257078 | 9/2006 |
| JP | 2007-052346 | 3/2007 |
| JP | 2007-86166 | 4/2007 |
| JP | 2007-145797 | 6/2007 |
| JP | 2007-161707 | 6/2007 |
| KR | 10-2007-0021974 | 2/2007 |
| WO | WO 2004/078703 | 9/2004 |

OTHER PUBLICATIONS

Kyung-Il Kim et al., "A New Route to 1,1-Difluoroolefins From Carboxylic Acids", Tetrahedron Letters, May 6, 1996, pp. 3223-3226, vol. 37, No. 19.

E. Chiellini et al., "Initiators-Poly-Reactions-Optical Activity", Springer-Verlag Berlin Heidelberg New York Tokyo 1984, pp. 2-49.

Li-Qing Hu et al., "Synthesis of Perhaloalkanesulfonyl Halides and Their Sulfonimide Derivatives", Inorganic Chemistry, 1993, pp. 5007-5010, vol. 32, No. 23.

International Search Report and the Written Opinion of the International Searching Authority for corresponding International Application No. PCT/JP2008/068533, Nov. 11, 2008.

Korean Office Action for corresponding KR Application No. 10-2010-7008086, Dec. 9, 2011.

Korean Office Action for corresponding KR Application No. 10-2010-7008086, Aug. 31, 2012.

* cited by examiner

*Primary Examiner* — Sin J. Lee

(74) *Attorney, Agent, or Firm* — Ditthavong Mori & Steiner, P.C.

(57) ABSTRACT

A compound has a partial structure shown by a following formula (1),

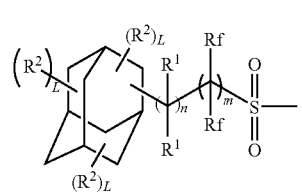

(1)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

10 Claims, No Drawings

COMPOUND, SALT, AND RADIATION-SENSITIVE RESIN COMPOSITION

CROSS-REFERENCE TO RELATED APPLICATIONS

The present application is a continuation application of International Application No. PCT/JP2008/068533, filed Oct. 14, 2008, which claims priority to Japanese Patent Application No. 2007-267700, filed Oct. 15, 2007. The contents of these applications are incorporated herein by reference in their entirety.

BACKGROUND OF THE INVENTION

1. Field of the Invention

The present invention relates to a compound, a salt, and a radiation-sensitive resin composition.

2. Discussion of the Background

In the field of microfabrication represented by production of integrated circuit devices, a lithographic process that enables microfabrication with a line width of 0.20 μm or less has been desired to achieve a higher degree of integration. A lithographic process has utilized near ultraviolet rays (e.g., i-line). However, it is difficult to implement sub-quarter-micron microfabrication using near ultraviolet rays.

Therefore, use of radiation having a shorter wavelength has been studied to enable microfabrication with a line width of 0.20 μm or less. Examples of such radiation include deep ultraviolet rays (e.g., mercury line spectrum and excimer laser light), X-rays, electron beams, and the like. In particular, technology that utilizes KrF excimer laser light (wavelength: 248 nm), ArF excimer laser light (wavelength: 193 nm), F2 excimer laser light (wavelength: 157 nm), EUV (wavelength: 13 nm), electron beams, or the like has attracted attention.

As a radiation-sensitive resin composition that is suitable for radiation having a short wavelength, various compositions (chemically-amplified radiation-sensitive compositions) that utilize a chemical amplification effect that occurs between an acid-dissociable functional group-containing component and a radiation-sensitive acid generator that generates an acid upon irradiation (exposure) have been proposed.

For example, Japanese Examined Patent Publication (KOKOKU) No. 2-27660 discloses a composition that includes a polymer containing a t-butyl ester group of a carboxylic acid or a t-butyl carbonate group of phenol, and a radiation-sensitive acid generator. This composition utilizes a phenomenon in which the t-butyl ester group or the t-butyl carbonate group contained in the polymer dissociates due to an acid generated upon exposure to form an acidic group (e.g., carboxyl group or phenolic hydroxyl group) so that the exposed area of the resist film becomes readily soluble in an alkaline developer.

A radiation-sensitive acid generator used for the chemically-amplified radiation-sensitive composition is required to exhibit high radiation transmittance, generate an acid having high acidity in high quantum yield, and ensure that the generated acid has an appropriate diffusion distance (diffusion length) in a resist film, and has high mutual solubility with an acid-dissociable group-containing resin, for example.

In order to generate an acid having high acidity, an appropriate diffusion length, and high mutual solubility with an acid-dissociable group-containing resin, the structure of an anionic moiety (ionic radiation-sensitive acid generator) or the structure of a sulfonyl moiety (nonionic radiation-sensitive acid generator having a sulfonyl structure or a sulfonate structure) is important. For example, a radiation-sensitive acid generator having a trifluoromethanesulfonyl structure or a nonafluorobutanesulfonyl structure generates a sufficiently strong acid so that the resulting photoresist exhibits sufficient sensitivity. However, since the acid generated by such a radiation-sensitive acid generator has a long diffusion length and poor mutual solubility with an acid-dissociable group-containing resin due to a high fluorine content, a deterioration in mask linearity, MEEF, and LWR occurs. On the other hand, a radiation-sensitive acid generator that has a sulfonyl structure bonded to a large organic group (e.g., 10-camphorsulfonyl structure) generates an acid that has a high carbon content, excellent mutual solubility with an acid-dissociable group-containing resin, and a sufficiently short diffusion length so that excellent mask linearity, MEEF, and LWR are achieved. However, since the acid generated by such a radiation-sensitive acid generator has insufficient acidity, the resulting photoresist exhibits poor sensitivity.

Therefore, development of a radiation-sensitive acid generator that may provide a chemically-amplified radiation-sensitive composition that has moderate sensitivity and exhibits excellent mask linearity, MEEF, and LWR in a well-balanced manner has been desired.

SUMMARY OF THE INVENTION

According to one aspect of the present invention, a compound includes a partial structure shown by a following formula (1),

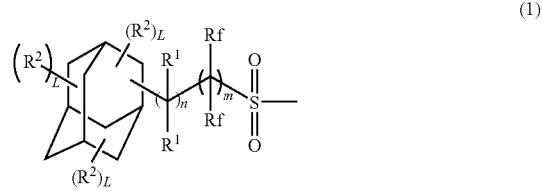

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

According to another aspect of the present invention, a salt is shown by a following formula (2),

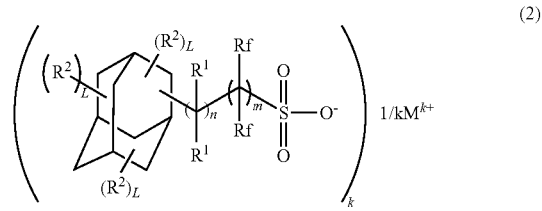

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, m represents an integer from 1 to 4, $M^{k+}$ represents a k-valent cation, and k represents an integer from 1 to 4.

According to another aspect of the present invention, a compound is shown by a following formula (3),

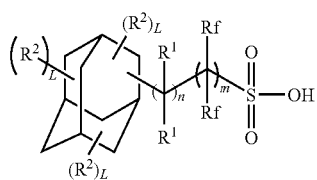

(3)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

According to another aspect of the present invention, a radiation-sensitive resin composition includes a compound including a partial structure shown and an acid-dissociable group-containing resin. The partial structure is shown by a following formula (1),

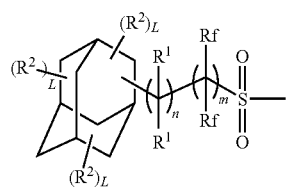

(1)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

According to another aspect of the present invention, a radiation-sensitive resin composition includes a salt and an acid-dissociable group-containing resin. The salt is shown by a following formula (2),

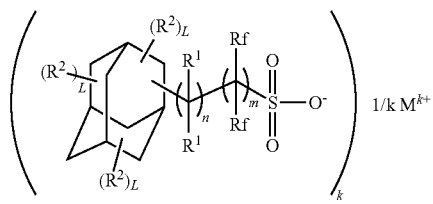

(2)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, m represents an integer from 1 to 4, $M^{k+}$ represents a k-valent cation, and k represents an integer from 1 to 4.

According to another aspect of the present invention, a radiation-sensitive resin composition includes a compound and an acid-dissociable group-containing resin. The compound is shown by a following formula (3),

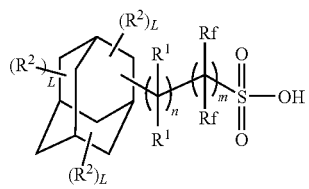

(3)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

According to another aspect of the present invention, a radiation-sensitive resin composition includes a salt and an acid-dissociable group-containing resin. The salt is shown by a following formula (2),

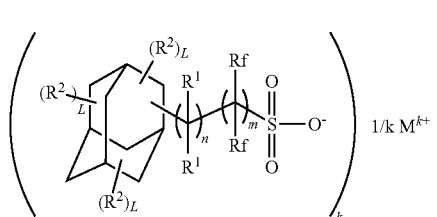

(2)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, m represents an integer from 1 to 4, $M^{k+}$ represents a k-valent cation, and k represents an integer from 1 to 4. The cation includes at least one of a sulfonium cation and an iodonium cation.

DESCRIPTION OF THE EMBODIMENTS

Preferred embodiments of the present invention are described below. Note that the present invention is not limited to the following embodiments. Various modifications and improvements may be made of the following embodiments within the scope of the present invention based on the knowledge of a person having ordinary skill in the art.

Compound

A compound according to one embodiment of the present invention has a partial structure shown by the following general formula (1).

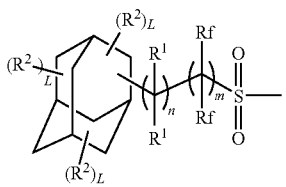

(1)

wherein R¹ represents a hydrogen atom or a substituted or unsubstituted hydrocarbon group having 1 to 8 carbon atoms, R² represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

The compound according to one embodiment of the present invention may be a polymer that has the structure shown by the general formula (1) in its repeating unit. Examples of the monomer that may be used as the repeating unit of the polymer include compounds that include at least one addition-polymerizable unsaturated bond and have the structure shown by the general formula (1) in the repeating unit, such as acrylates, acrylamides, methacrylates, methacrylamides, allyl compounds, vinyl ethers, vinyl esters, styrenes, and crotonates.

The compound according to one embodiment of the present invention may be a compound that has the structure shown by the general formula (1) and does not include a repeating unit. The term "compound that has the structure shown by the general formula (1) and does not include a repeating unit" refers to a compound that does not include a polymerizable repeating unit and has a polystyrene-reduced weight average molecular weight determined by gel permeation chromatography (GPC) of 1000 or less. It is preferable that the partial structure shown by the general formula (1) has a high carbon content from the viewpoint of mutual solubility with a resin. Specifically, R¹ and R² may be a hydrogen atom.

Specific examples of the compound that may have the structure shown by the general formula (1) include trihalomethyl-s-triazines, trihalomethyloxadizoles, hexaarylbiimidazoles, organic peroxides, triarylalkyl borates, ethanolamines, N-phenylglycines, N-trimethylsilylmethylanilines, 2-alkyl-1-[4-(alkylthio)phenyl]-2-morpholinopropanone-1, oxime ethers, 2-mercaptobenzthiazoles, 2-mercaptobenzoxazoles, 2-mercaptobenzimidazoles, disulfones, N-hydroxyimides, glyoximes, β-ketosulfone acids, sulfonates, and the like. These compounds readily generate active radicals and acids.

Since the compound according to one embodiment of the present invention has a strong fluorine-containing electron-attracting group at the α-position of the sulfonyl group contained in the structure (1), an acid generated by the compound has high acidity. Moreover, the diffusion length within a resist film is moderately short due to a high carbon content.

The compound according to one embodiment of the present invention generates a sulfonic acid shown by the following general formula (3) upon exposure or heating.

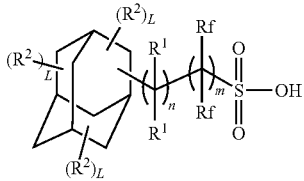

(3)

wherein R¹ represents a hydrogen atom or a substituted or unsubstituted hydrocarbon group having 1 to 8 carbon atoms, R² represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, and m represents an integer from 1 to 4.

It is preferable that the partial structure shown by the general formula (1) has a high carbon content from the viewpoint of mutual solubility with a resin. Specifically, R¹ and R² may be a hydrogen atom.

Examples of a preferable ionic compound among the compounds shown by the general formula (1) include a sulfonate shown by the following general formula (2).

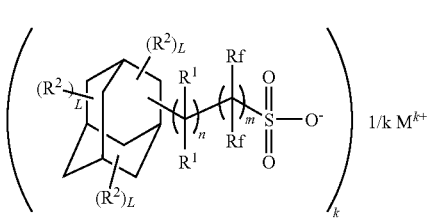

(2)

wherein R¹ represents a hydrogen atom or a substituted or unsubstituted hydrocarbon group having 1 to 8 carbon atoms, R² represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents an integer from 0 to 10, m represents an integer from 1 to 4, $M^{k+}$ represents a k-valent cation, and k represents an integer from 1 to 4.

Examples of the monovalent onium cation represented by $M^+$ (k=1) in the general formula (2) include onium cations of O, S, Se, N, P, As, Sb, Cl, Br, I, and the like. Among these onium cations, a sulfonium cation and an iodonium cation are preferable.

Examples of the sulfonium cation and the iodonium cation among the monovalent onium cations represented by $M^+$ in the general formula (2) include sulfonium cations shown by the following general formula (1) and iodonium cations shown by the following general formula (ii), respectively.

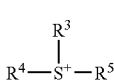

(i)

wherein $R^3$, $R^4$, and $R^5$ represents a substituted or unsubstituted linear or branched alkyl group having 1 to 10 carbon atoms or a substituted or unsubstituted aryl group having 6 to 18 carbon atoms, provided that at least two of $R^3$, $R^4$, and $R^5$ may bond to form a ring with the sulfur atom.

$$R^6\text{—}I^+\text{—}R^7 \quad (ii)$$

wherein $R^6$ and $R^7$ represents a substituted or unsubstituted linear or branched alkyl group having 1 to 10 carbon atoms or a substituted or unsubstituted aryl group having 6 to 18 carbon atoms, provided that $R^6$ and $R^7$ may bond to form a ring with the iodine atom.

The monovalent onium cation represented by $M^+$ may be produced by the method described in Advances in Polymer Science, vol. 62, pp. 1-48 (1984), for example.

Examples of a preferable monovalent onium cation include sulfonium cations shown by the following formulas (i-1) to (i-64), iodonium cations shown by the following formulas (ii-1) to (ii-39), and the like.

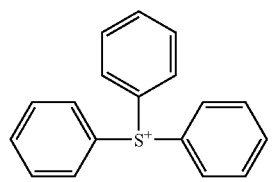 (i-1)

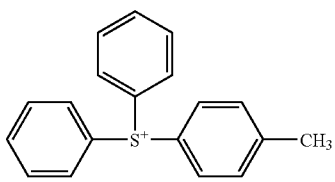 (i-2)

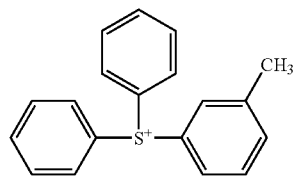 (i-3)

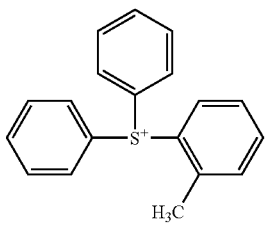 (i-4)

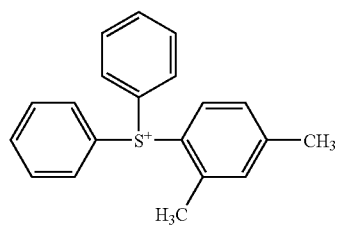 (i-5)

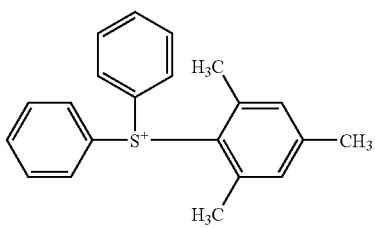 (i-6)

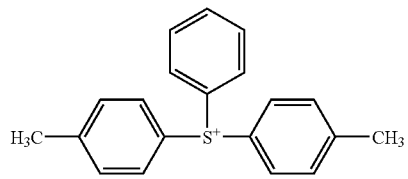 (i-7)

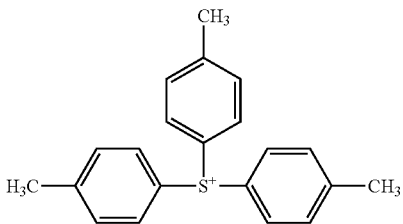 (i-8)

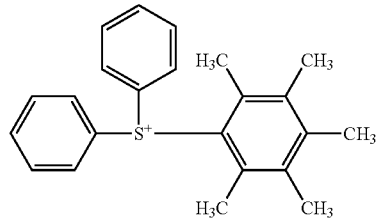 (i-9)

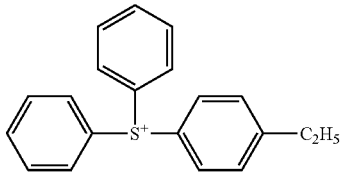 (i-10)

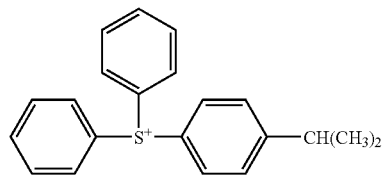 (i-11)

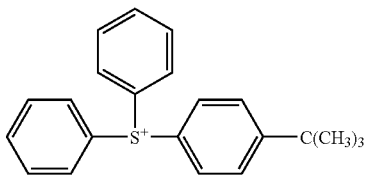 (i-12)

-continued
(i-13)
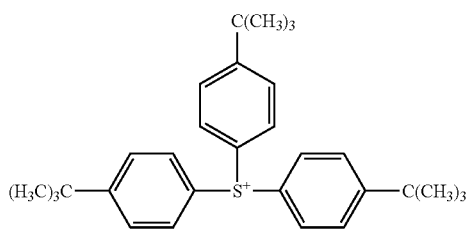
(i-14)
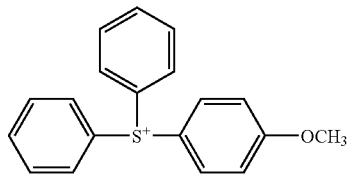
(i-15)
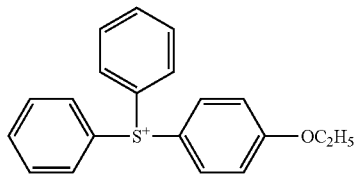
(i-16)
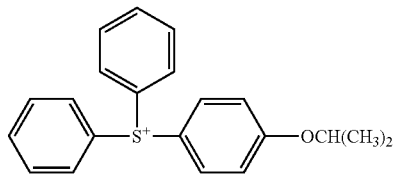
(i-17)
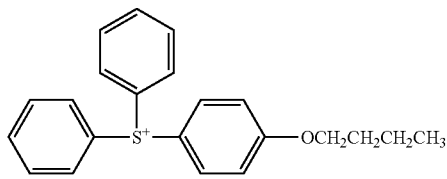
(i-18)
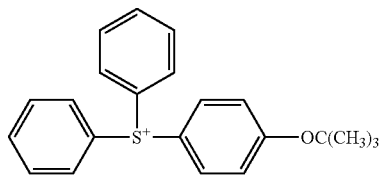
(i-19)
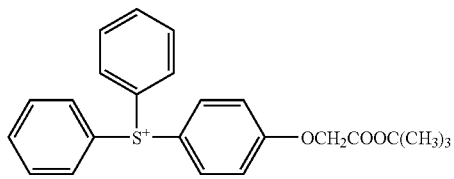
(i-20)
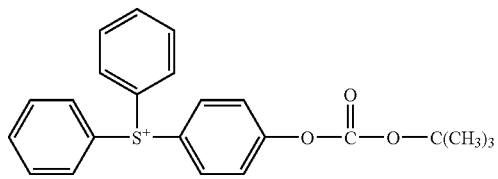
(i-21)
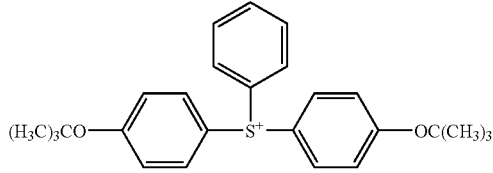
(i-22)
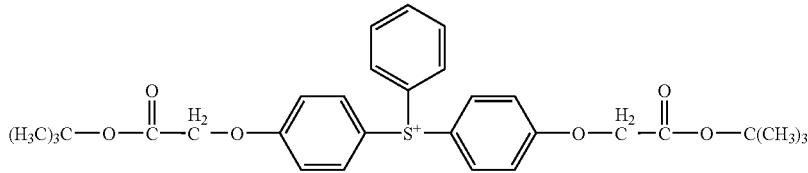
(i-23)
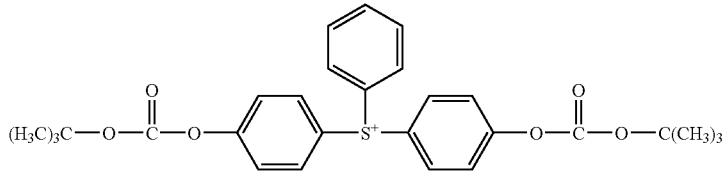
(i-24)
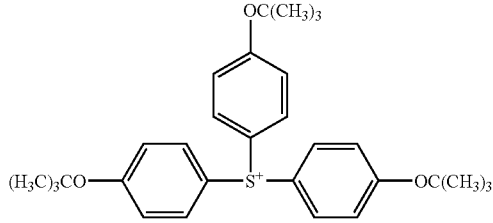

-continued
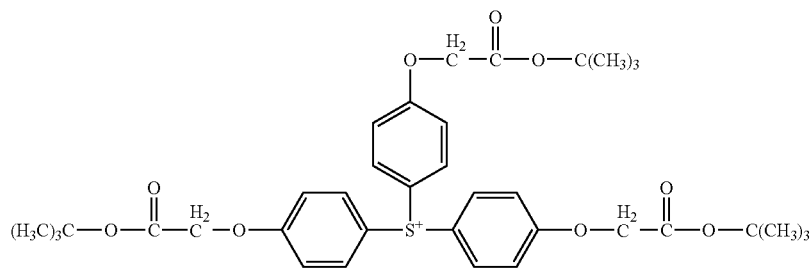
(i-25)
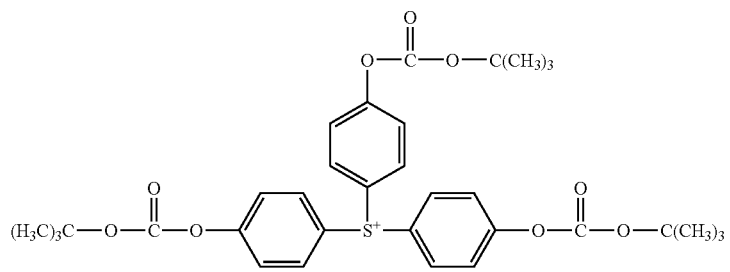
(i-26)
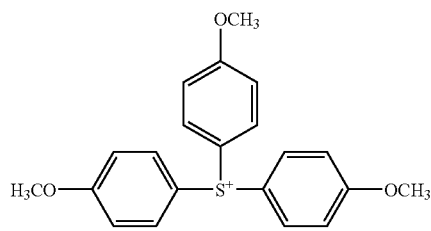
(i-27)
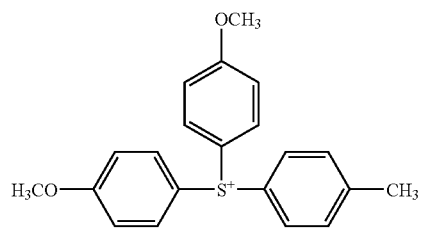
(i-28)
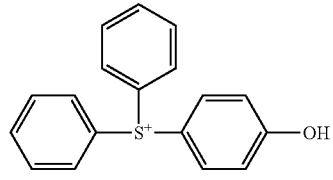
(i-29)
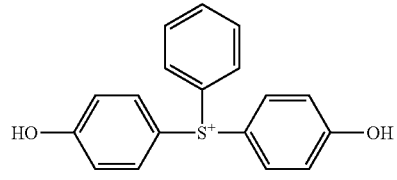
(i-30)
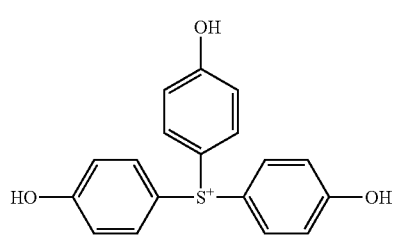
(i-31)
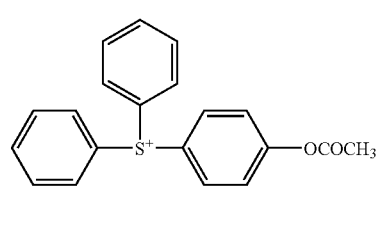
(i-32)
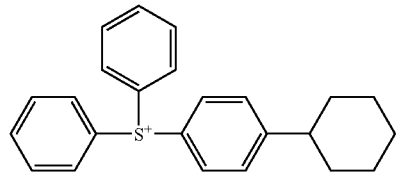
(i-33)
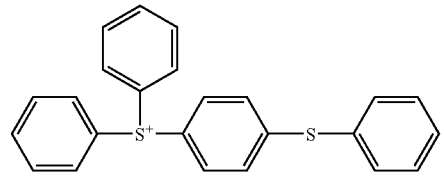
(i-34)
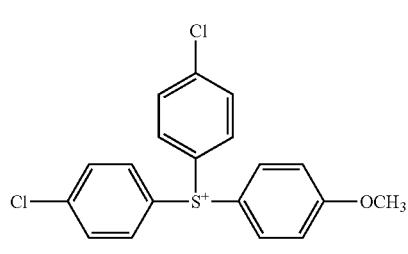
(i-35)
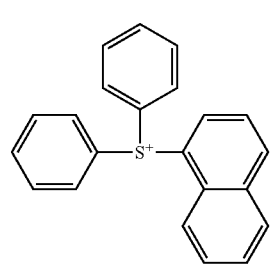
(i-36)

-continued
(i-37) 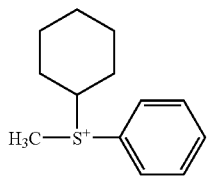
(i-38) 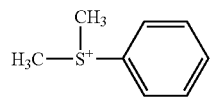
(i-39) 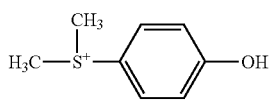
(i-40) 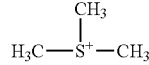
(i-41) 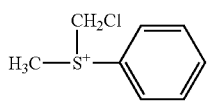
(i-42) 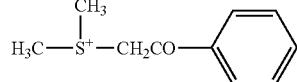
(i-43) 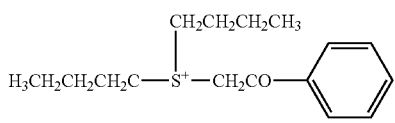
(i-44) 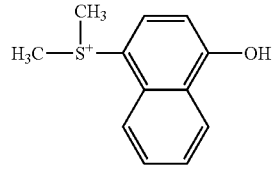
(i-45) 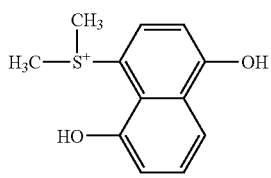
(i-46) 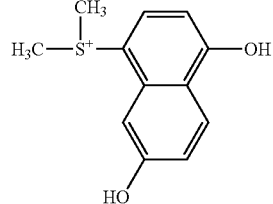
(i-47) 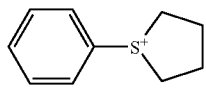
(i-48) 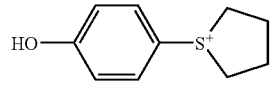
(i-49) 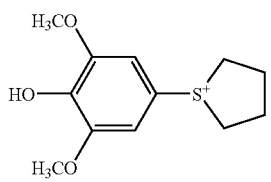
(i-50) 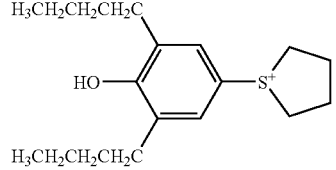
(i-51) 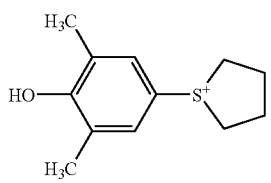
(i-52) 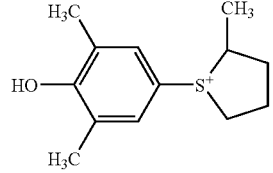
(i-53) 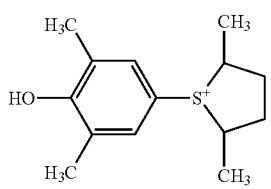
(i-54) 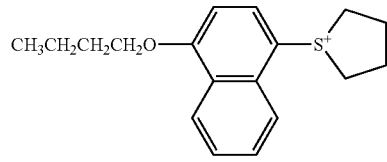

-continued
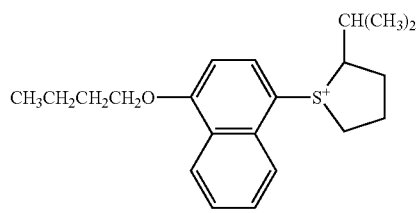
(i-55)
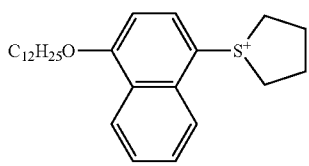
(i-56)
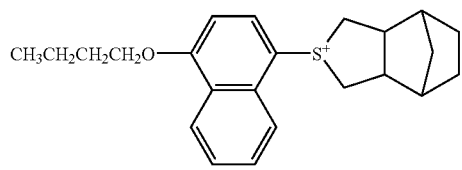
(i-57)
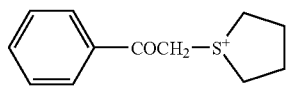
(i-58)
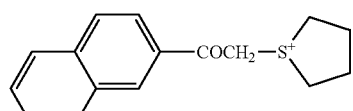
(i-59)
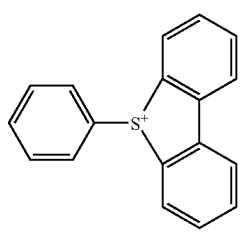
(i-60)
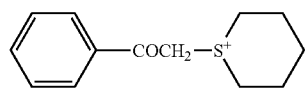
(i-61)
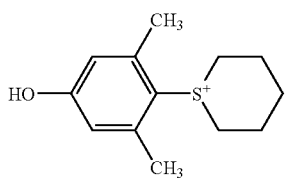
(i-62)
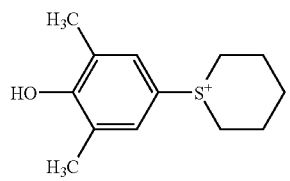
(i-63)
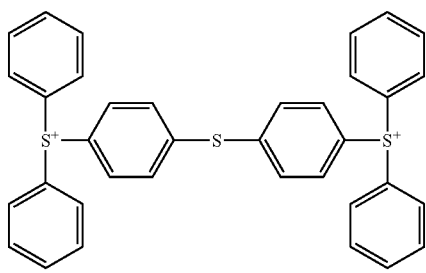
(i-64)
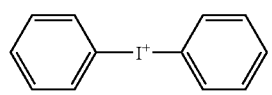
(ii-1)
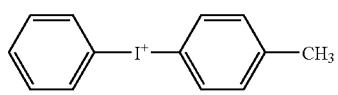
(ii-2)
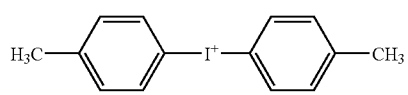
(ii-3)
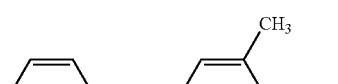
(ii-4)
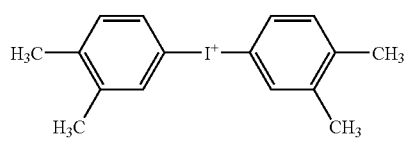
(ii-5)
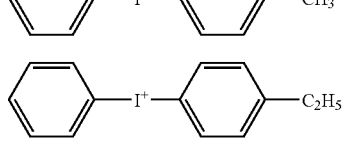
(ii-6)
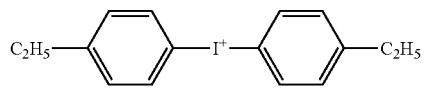
(ii-7)
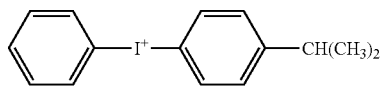
(ii-8)
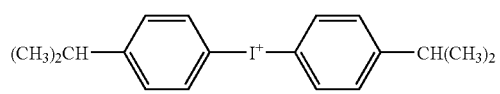
(ii-9)
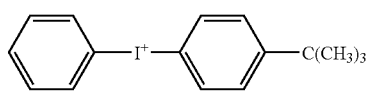
(ii-10)

-continued
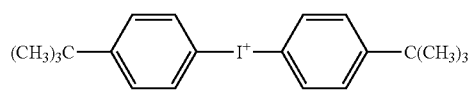 (ii-11)
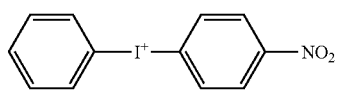 (ii-12)
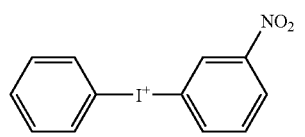 (ii-13)
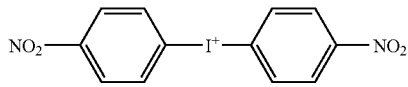 (ii-14)
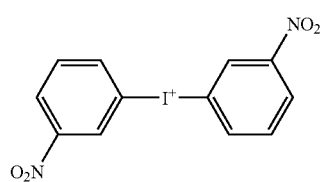 (ii-15)
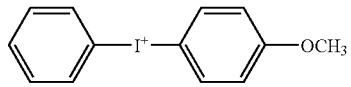 (ii-16)
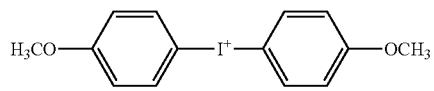 (ii-17)
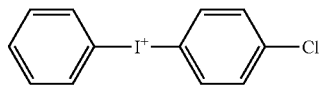 (ii-18)
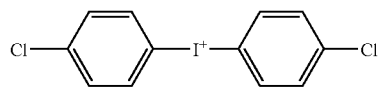 (ii-19)
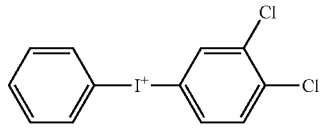 (ii-20)
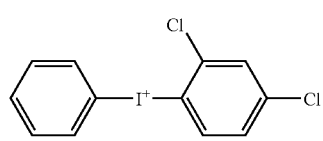 (ii-21)
 (ii-22)
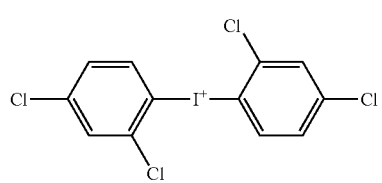 (ii-23)
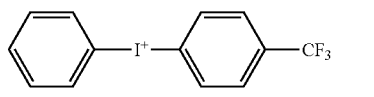 (ii-24)
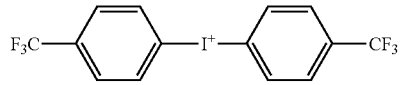 (ii-25)
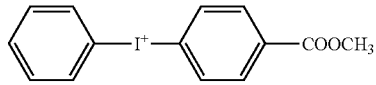 (ii-26)
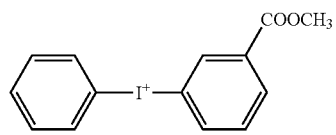 (ii-27)
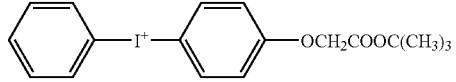 (ii-28)
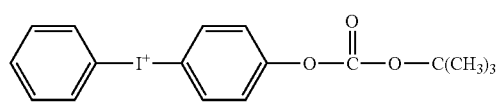 (ii-29)
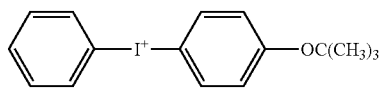 (ii-30)
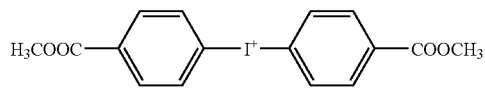 (ii-31)
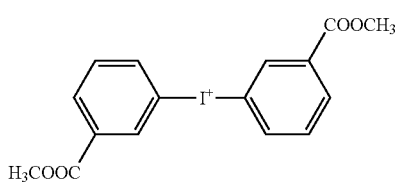 (ii-32)
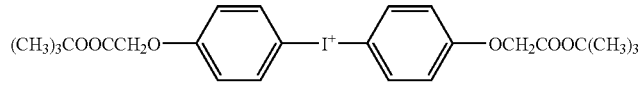 (ii-33)

-continued

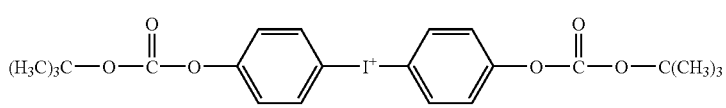
(ii-34)

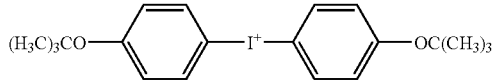
(ii-35)

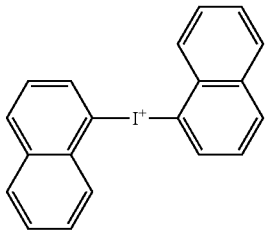
(ii-36)

(ii-37)

(ii-38)

(ii-39)

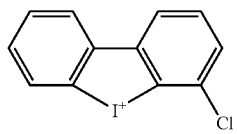

Among these monovalent onium cations, the sulfonium cations shown by the formulas (i-1), (i-2), (i-6), (i-8), (i-13), (i-19), (i-25), (i-27), (i-29), (i-33), (i-51), and (i-54), the iodonium cations shown by the formulas (ii-1) and (ii-11), and the like are preferable.

Production Method

The onium sulfonate compound shown by the general formula (2) may be synthesized by the method described in Advances in Polymer Science, vol. 62, pp. 1-48 (1984) or Inorganic Chemistry, vol. 32, pp. 5007-5010 (1993), for example. As shown by the following reaction formula [1], a precursor compound (1a) is reacted with sodium dithionite in the presence of an inorganic base to produce a sulfinate (1b). The sulfinate (1b) is oxidized using an oxidizing agent such as hydrogen peroxide to produce a sulfonate (1c). The sulfonate (1c) is subjected to an ion-exchange reaction with a counterion exchange precursor $M^+Z^-$ to produce the onium sulfonate compound shown by the general formula (2).

[1]

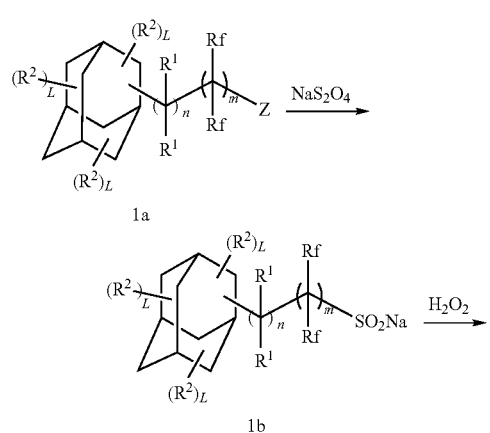

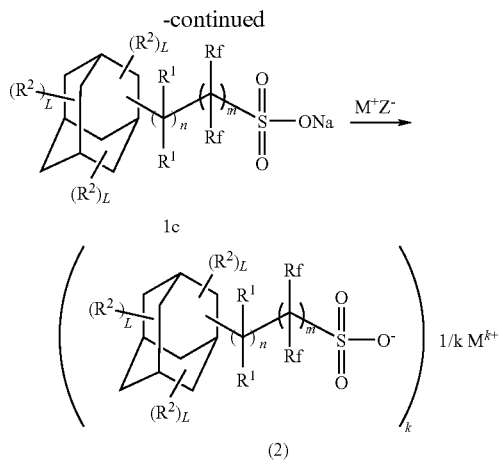

wherein Z represents a monovalent leaving group, and $Z^-$ represents a monovalent anion.

Examples of the monovalent leaving group represented by Z contained in the precursor (1a) include halogen atoms such as a chlorine atom, a bromine atom, and an iodine atom, a methanesulfonate group, a p-toluenesulfonate group, and the like. Among these, a bromine atom, an iodine atom, and the like are preferable.

When reacting the precursor compound (1a) with sodium dithionite, the molar ratio of sodium dithionite to the precursor compound (1a) is normally 0.01 to 100, and preferably 1.0 to 10.

Examples of the inorganic base used in the above reaction include lithium carbonate, sodium carbonate, potassium carbonate, lithium hydrogen carbonate, sodium hydrogen carbonate, potassium hydrogen carbonate, and the like. Among these, sodium hydrogen carbonate, potassium hydrogen carbonate, and the like are preferable. These inorganic bases may be used either individually or in combination. The molar ratio of the inorganic base to sodium dithionite is normally 1.0 to 10.0, and preferably 2.0 to 4.0.

The above reaction is preferably carried out in a mixed solvent that contains an organic solvent and water. As the organic solvent, it is preferable to use a solvent that exhibits high mutual solubility with water, such as a lower alcohol, tetrahydrofuran, N,N-dimethylformamide, N,N-dimethylacetoamide, acetonitrile, or dimethylsulfoxide. Among these, N,N-dimethylacetoamide, acetonitrile, and dimethylsulfoxide are more preferable, with acetonitrile and dimethyl sulfoxide being particularly preferable. These organic solvents may be used either individually or in combination. The organic solvent used is normally used in an amount of 5 parts by mass or more, preferably 10 parts by mass or more, and more preferably 20 to 90 parts by mass, based on 100 parts by mass of the organic solvent and water in total. The mixed solvent is normally used in an amount of 5 to 100 parts by mass, preferably 10 to 100 parts by mass, and more preferably 20 to 90 parts by mass, based on 100 parts by mass of the precursor compound (1a).

The reaction temperature is normally 40 to 200° C., and preferably 60 to 120° C., and the reaction time is normally 0.5 to 72 hours, and preferably 2 to 24 hours. A pressure vessel such as an autoclave is used when the reaction temperature is set to be higher than the boiling point of the organic solvent or water.

Examples of the oxidizing agent used when oxidizing the sulfinate (1b) include hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmium (VII) oxide, ruthenium (VII) oxide, sodium hypochlorite, sodium chlorite, oxygen gas, ozone gas, and the like. Among these, hydrogen peroxide, methachloroperbenzoic acid, t-butyl hydroperoxide, and the like are preferable. These oxidizing agents may be used either individually or in combination. The molar ratio of the oxidizing agent to the sulfinate (1b) is normally 1.0 to 10.0, and preferably 1.5 to 4.0.

A transition metal catalyst may be used in combination with the oxidizing agent. Examples of the transition metal catalyst include disodium tungstate, iron (III) chloride, ruthenium (III) chloride, selenium (IV) chloride, and the like. Among these, disodium tungstate is preferable. These transition metal catalysts may be used either individually or in combination. The molar ratio of the transition metal catalyst to the sulfinate (1b) is normally 0.001 to 2.0, preferably 0.01 to 1.0, and more preferably 0.03 to 0.5.

A buffer may be used in combination with the oxidizing agent and the transition metal catalyst in order to adjust the pH of the reaction solution. Examples of the buffer include disodium hydrogen phosphate, sodium dihydrogen phosphate, dipotassium hydrogen phosphate, potassium dihydrogen phosphate, and the like. These buffers may be used either individually or in combination. The molar ratio of the buffer to the sulfinate (1b) is normally 0.01 to 2.0, preferably 0.03 to 1.0, and more preferably 0.05 to 0.5.

The above reaction is normally carried out in a reaction solvent. As the reaction solvent, it is preferable to use water or an organic solvent such as a lower alcohol, tetrahydrofuran, N,N-dimethylformamide, N,N-dimethylacetoamide, acetonitrile, dimethylsulfoxide, acetic acid, or trifluoroacetic acid. Among these, water, methanol, N,N-dimethylacetoamide, acetonitrile, and dimethylsulfoxide are more preferable, with water and methanol being particularly preferable. These organic solvents may be used either individually or in combination. If necessary, the organic solvent and water may be used in combination. In this case, the organic solvent is normally used in an amount of 5 parts by mass or more, preferably 10 parts by mass or more, and more preferably 20 to 90 parts by mass, based on 100 parts by mass of the organic solvent and water in total. The reaction solvent is normally used in an amount of 5 to 100 parts by mass, preferably 10 to 100 parts by mass, and particularly preferably 20 to 50 parts by mass, based on 100 parts by mass of the sulfinate (1b).

The reaction temperature is normally 0 to 100° C., preferably 5 to 60° C., and more preferably 5 to 40° C., and the reaction time is normally 0.5 to 72 hours, and preferably 2 to 24 hours.

The sulfonate (1c) may be subjected to an ion-exchange reaction by the method described in J. Photopolym. Sci. Tech., pp. 571-576 (1998), ion-exchange chromatography, or the method described in each synthesis example, for example.

Examples of the monovalent anion represented by $Z^-$ in the reaction formula (1) include $F^-$, $Cl^-$, $Br^-$, $I^-$, a perchlorate ion, a hydrogen sulfurate ion, a dihydrogen phosphorate ion, a tetrafluoroborate ion, an aliphatic sulfonate ion, an aromatic sulfonate ion, a trifluoromethane sulfonate ion, a fluorosulfonate ion, a hexafluorophosphate ion, a hexachloroantimonate ion, and the like. Among these, $Cl^-$, $Br^-$, a hydrogen sulfurate ion, a tetrafluoroborate ion, an aliphatic sulfonate ion are preferable, with Cl, Br, and a hydrogen sulfurate ion being particularly preferable. The molar ratio of the counter-ion exchange precursor to the sulfonate (1c) is normally 0.1 to 10.0, preferably 0.3 to 4.0, and more preferably 0.7 to 2.0.

The above reaction is normally carried out in a reaction solvent. As the reaction solvent, it is preferable to use water or an organic solvent such as a lower alcohol, tetrahydrofuran, N,N-dimethylformamide, N,N-dimethylacetoamide, acetonitrile, or dimethylsulfoxide. Among these, water, methanol, N,N-dimethylacetoamide, acetonitrile, and dimethylsulfoxide are more preferable, with water being particularly preferable. These organic solvents may be used either individually or in combination. If necessary, water and the organic solvent may be used in combination. In this case, the organic solvent is normally used in an amount of 5 parts by mass or more, preferably 10 parts by mass or more, and more preferably 20 to 90 parts by mass, based on 100 parts by mass of water and the organic solvent in total. The reaction solvent is normally used in an amount of 5 to 100 parts by mass, preferably 10 to 100 parts by mass, and particularly preferably 20 to 50 parts by mass, based on 100 parts by mass of the counter-ion exchange precursor.

The reaction temperature is normally 0 to 80° C., and preferably from 5 to 30° C., and the reaction time is normally 10 minutes to 6 hours, and preferably 30 minutes to 2 hours.

The onium sulfonate compound (2) thus obtained may be purified by extraction using an organic solvent. As the organic solvent used for purification, it is preferable to use an organic solvent that is immiscible with water, such as an ester (e.g., ethyl acetate or n-butyl acetate), an ether (e.g., diethyl ether), or an alkyl halide (e.g., methylene chloride or chloroform). These organic solvents may be used either individually or in combination.

As shown by the following reaction formula [2], a precursor compound (2a) is converted into a precursor compound (2b) by reacting the precursor compound (2a) with dimethyl-2,2-azobisbutyrate and triethylamine with heating, for example. The precursor compound (2b) is subjected to a halogenation transfer reaction, and reacted with an organo-copper reagent to obtain a precursor compound (1a).

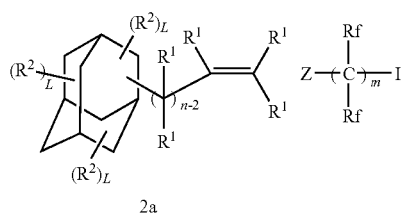

2a adamantane derivative (3a) is reacted with carbon monoxide to synthesize an adamantane derivative (3b). After optionally adjusting the position of the added carbon monoxide by thermal rearrangement, the adamantane derivative (3b) is subjected to a difluoro-Wittig reaction in a reaction solvent using dibromodifluoromethane and triphenylphosphine or tris(dimethylamino)phosphine in the presence of zinc to obtain a corresponding olefin compound (3c). A hydrogen halide (HZ) other than hydrogen fluoride is then added to the olefin compound (3c) in a reaction solvent (see 1a-1 and 1a-2 in the reaction formula [3]).

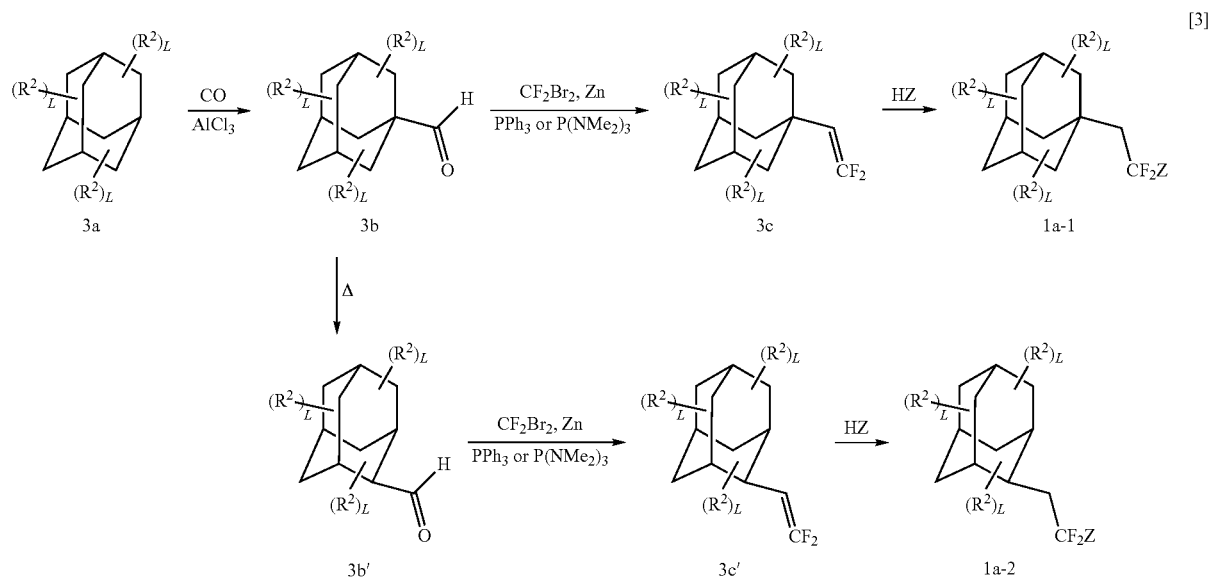

-continued

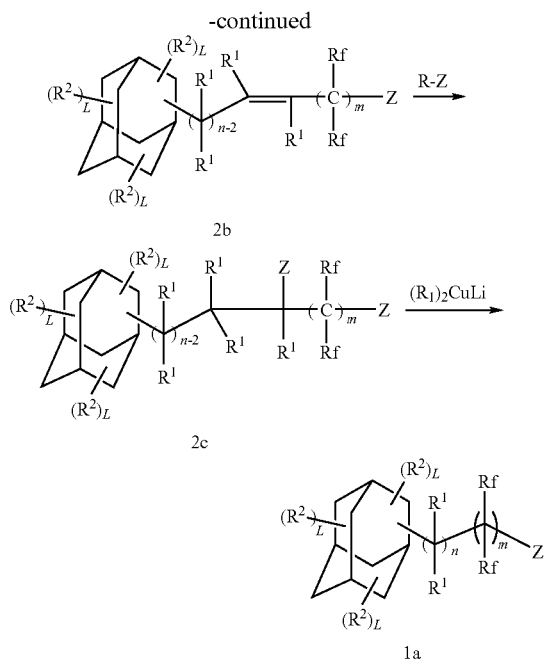

The precursor compound (1a) may also be obtained as shown by the following reaction formula [3]. Specifically, an Positive-tone radiation-sensitive resin composition and negative-tone radiation-sensitive resin composition
Radiation-Sensitive Acid Generator A positive-tone radiation-sensitive resin composition and a negative-tone radiation-sensitive resin composition according to one embodiment of the present invention include a radiation-sensitive acid generator that includes a sulfone compound having a structure shown by the general formula (1), a sulfonate having a structure shown by the general formula (2), and/or a sulfonic acid having a structure shown by the general formula (3). In the positive-tone radiation-sensitive resin composition and the negative-tone radiation-sensitive resin composition according to one embodiment of the present invention, the radiation-sensitive acid generators may be used either individually or in combination.

In the positive-tone radiation-sensitive resin composition and the negative-tone radiation-sensitive resin composition according to one embodiment of the present invention, the radiation-sensitive acid generator having a structure shown by the general formula (1) is normally used in an amount of 0.1 to 20 parts by mass, preferably 0.1 to 15 parts by mass, and more preferably 0.2 to 12 parts by mass, based on 100 parts by mass of an acid-dissociable group-containing resin or an alkali-soluble resin, although the amount of the radiation-sensitive acid generator varies depending on the type of radiation-sensitive acid generator or the type of additional acid generator. If the amount of the radiation-sensitive acid generator is less than 0.1 parts by mass, the desired effects of the embodiment of the present invention may not be sufficiently achieved. If the amount of the radiation-sensitive acid generator is more than 20 parts by mass, the radiation transmittance, the pattern shape, the heat resistance, and the like of the composition may decrease.

The positive-tone radiation-sensitive resin composition and the negative-tone radiation-sensitive resin composition according to one embodiment of the present invention may include at least one radiation-sensitive acid generator (hereinafter referred to as "additional acid generator") other than the radiation-sensitive acid generator that includes a sulfone compound shown by the general formula (1).

Examples of the additional acid generator include onium salt compounds, sulfone compounds, sulfonate compounds, sulfonimide compounds, diazomethane compounds, disulfonylmethane compounds, oxime sulfonate compound, hydrazine sulfonate compounds, and the like.

Examples of the onium salt compounds include iodonium salts, sulfonium salts (including tetrahydrothiophenium salts), phosphonium salts, diazonium salts, ammonium salts, pyridinium salts, and the like. Examples of the sulfone compounds include β-ketosulfone, β-sulfonylsulfone, α-diazo compounds thereof, and the like. Examples of the sulfonate compounds include alkyl sulfonates, haloalkyl sulfonates, aryl sulfonates, imino sulfonates, and the like. Examples of the sulfonimide compounds include compounds shown by the following general formula (4).

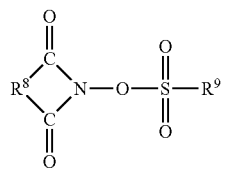
(4)

wherein $R^8$ represents a divalent organic group, and $R^9$ represents a monovalent organic group.

Examples of the divalent organic group represented by $R^8$ in the general formula (4) include a methylene group, a linear or branched alkylene group having 2 to 20 carbon atoms, an aralkylene group having 7 to 20 carbon atoms, a difluoromethylene group, a linear or branched perfluoroalkylene group having 2 to 20 carbon atoms, a cyclohexylene group, a phenylene group, a divalent group having a norbornane skeleton, a group in which any of these groups is substituted with an aryl group having 6 or more carbon atoms or an alkoxy group having 1 or more carbon atoms, and the like.

Examples of the monovalent organic group represented by $R^9$ include a linear or branched alkyl group having 1 to 10 carbon atoms, a linear or branched perfluoroalkyl group having 1 to 10 carbon atoms, a perfluorocycloalkyl group having 3 to 10 carbon atoms, a bicyclo ring-containing monovalent hydrocarbon group having 7 to 15 carbon atoms, an aryl group having 6 to 12 carbon atoms, and the like.

Examples of the diazomethane compounds include compounds shown by the following general formula (5).

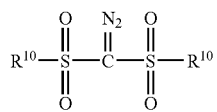
(5)

wherein $R^{10}$ represents a monovalent group such as a linear or branched alkyl group, a cycloalkyl group, an aryl group, a halogen-substituted alkyl group, a halogen-substituted cycloalkyl group, or a halogen-substituted aryl group.

Examples of the disulfonylmethane compounds include compounds shown by the following general formula (6).

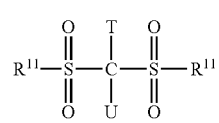
(6)

wherein $R^{11}$ represents a linear or branched monovalent aliphatic hydrocarbon group, a cycloalkyl group, an aryl group, an aralkyl group, or a monovalent organic group having a hetero atom, and T and U individually represent an aryl group, a hydrogen atom, a linear or branched monovalent aliphatic hydrocarbon group, a cycloalkyl group, an aralkyl group, or a monovalent organic group having a hetero atom, provided that one of T and U is an aryl group, or T and U bond to form a monocyclic or polycyclic ring having at least one unsaturated bond, or T and U bond to form a group shown by the following general formula (7).

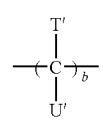
(7)

wherein T' and U' individually represent a hydrogen atom, a halogen atom, a linear or branched alkyl group, a cycloalkyl group, an aryl group, or an aralkyl group, or T' and U' that are bonded to an identical carbon atom or different carbon atoms form a monocyclic carbon structure, and b represents an integer from 2 to 10.

Examples of the oxime sulfonate compounds include compounds shown by the following general formulas (8-1) and (8-2) and the like.

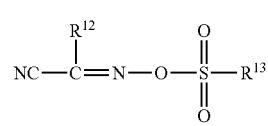
(8-1)

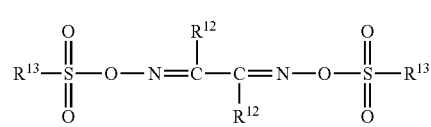
(8-2)

wherein $R^{12}$ and $R^{13}$ individually represent a monovalent organic group. A plurality of $R^{12}$ and a plurality of $R^{13}$ present in the general formula (8-2) may respectively be either the same or different.

Specific examples of the monovalent organic group represented by $R^{12}$ in the general formulas (8-1) and (8-2) include a methyl group, an ethyl group, an n-propyl group, a phenyl group, a p-tolyl group, and the like.

Specific examples of the monovalent organic group represented by $R^{13}$ include a phenyl group, a p-tolyl group, a 1-naphthyl group, and the like.

Examples of the hydrazine sulfonate compounds include compounds shown by the following general formulas (9-1) and (9-2) and the like.

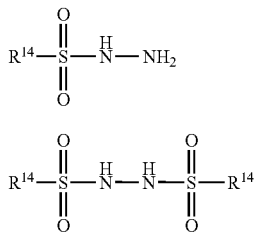

wherein $R^{14}$ represents a monovalent organic group. A plurality of $R^{14}$ present in the general formula (9-2) may be either the same or different.

Specific examples of the monovalent organic group represented by $R^{14}$ in the general formulas (9-1) and (9-2) include a methyl group, an ethyl group, an n-propyl group, a phenyl group, a p-tolyl group, a trifluoromethyl group, a nonafluoro-n-butyl group, and the like.

The additional acid generator preferably includes at least one compound selected from the group consisting of the onium salt compounds, the sulfonimide compounds, and the diazomethane compounds.

Examples of particularly preferable additional acid generators include
diphenyliodonium trifluoromethanesulfonate,
diphenyliodonium nonafluoro-n-butanesulfonate,
diphenyliodonium p-toluenesulfonate, diphenyliodonium 10-camphorsulfonate,
diphenyliodonium 2-trifluoromethylbenzenesulfonate,
diphenyliodonium 4-trifluoromethylbenzenesulfonate,
diphenyliodonium 2,4-difluorobenzenesulfonate,
diphenyliodonium 1,1,2,2-tetrafluoro-2-(norbornan-2-yl)ethanesulfonate, diphenyliodonium 2-(5-t-buthoxycarbonyloxybicyclo[2.2.1]heptan-2-yl)-1,1,2,2-tetrafluoroethanesulfonate,
diphenyliodonium 2-(6-t-buthoxycarbonyloxybicyclo[2.2.1]heptan-2-yl)-1,1,2,2-tetrafluoroethanesulfonate,
diphenyliodonium 1,1-difluoro-2-(bicyclo[2.2.1]heptan-2-yl)ethanesulfonate,
bis(4-t-butylphenyl)iodonium trifluoromethanesulfonate,
bis(4-t-butylphenyl)iodonium nonafluoro-n-butanesulfonate, bis(4-t-butylphenyl)iodonium p-toluenesulfonate,
bis(4-t-butylphenyl)iodonium 10-camphorsulfonate,
bis(4-t-butylphenyl)iodonium 2-trifluoromethylbenzenesulfonate,
bis(4-t-butylphenyl)iodonium 4-trifluoromethylbenzenesulfonate,
bis(4-t-butylphenyl)iodonium 2,4-difluorobenzenesulfonate, bis(4-t-butylphenyl)iodonium 1,1,2,2-tetrafluoro-2-(norbornan-2-yl)ethanesulfonate, bis(4-t-butylphenyl)iodonium 1,1-difluoro-2-(bicyclo[2.2.1]heptan-2-yl)
ethanesulfonate,
triphenylsulfonium trifluoromethanesulfonate,
triphenylsulfonium nonafluoro-n-butanesulfonate,
triphenylsulfonium p-toluenesulfonate, triphenylsulfonium 10-camphorsulfonate,
triphenylsulfonium 2-trifluoromethylbenzenesulfonate,
triphenylsulfonium 4-trifluoromethylbenzenesulfonate,
triphenylsulfonium 2,4-difluorobenzenesulfonate,
triphenylsulfonium 1,1,2,2-tetrafluoro-2-(norbornan-2-yl)ethanesulfonate, triphenylsulfonium 2-(5-t-buthoxycarbonyloxybicyclo[2.2.1]heptan-2-yl)-1,1,2,2-tetrafluoroethanesulfonate,
triphenylsulfonium 2-(6-t-buthoxycarbonyloxybicyclo[2.2.1]heptan-2-yl)-1,1,2,2-tetrafluoroethanesulfonate,
triphenylsulfonium 2-(5-pivaloyloxybicyclo[2.2.1]heptan-2-yl)-1,1,2,2-tetrafluoroethanesulfonate,
triphenylsulfonium 2-(6-pivaloyloxybicyclo[2.2.1]heptan-2-yl)-1,1,2,2-tetrafluoroethanesulfonate,
triphenylsulfonium 2-(5-hydroxybicyclo[2.2.1]heptan-2-yl)-1,1,2,2-tetrafluoroethanesulfonate,
triphenylsulfonium 2-(6-hydroxybicyclo[2.2.1]heptan-2-yl)-1,1,2,2-tetrafluoroethanesulfonate,
triphenylsulfonium 2-(5-methanesulfonyloxybicyclo[2.2.1]heptan-2-yl)-1,1,2,2-tetrafluoroethanesulfonate,
triphenylsulfonium 2-(6-methanesulfonyloxybicyclo[2.2.1]heptan-2-yl)-1,1,2,2-tetrafluoroethanesulfonate,
triphenylsulfonium 2-(5-i-propanesulfonyloxybicyclo[2.2.1]heptan-2-yl)-1,1,2,2-tetrafluoroethanesulfonate,
triphenylsulfonium 2-(6-i-propanesulfonyloxybicyclo[2.2.1]heptan-2-yl)-1,1,2,2-tetrafluoroethanesulfonate,
triphenylsulfonium 2-(5-n-hexanesulfonyloxybicyclo[2.2.1]heptan-2-yl)-1,1,2,2-tetrafluoroethanesulfonate,
triphenylsulfonium 2-(6-n-hexanesulfonyloxybicyclo[2.2.1]heptan-2-yl)-1,1,2,2-tetrafluoroethanesulfonate,
triphenylsulfonium 2-(5-oxobicyclo[2.2.1]heptan-2-yl)-1,1,2,2-tetrafluoroethanesulfonate,
triphenylsulfonium 2-(6-oxobicyclo[2.2.1]heptan-2-yl)-1,1,2,2-tetrafluoroethanesulfonate,
triphenylsulfonium 1,1-difluoro-2-(bicyclo[2.2.1]heptan-2-yl)ethanesulfonate,
1-(4-n-butoxynaphthalen-1-yl)tetrahydrothiophenium trifluoromethanesulfonate,
1-(4-n-butoxynaphthalen-1-yl)tetrahydrothiophenium nonafluoro-n-butanesulfonate,
1-(4-n-butoxynaphthalen-1-yl)tetrahydrothiophenium 1,1,2,2-tetrafluoro-2-(norbornan-2-yl)ethanesulfonate,
1-(4-n-butoxynaphthalen-1-yl)tetrahydrothiophenium 2-(5-t-buthoxycarbonyloxybicyclo[2.2.1]heptan-2-yl)-1,1,2,2-tetrafluoroethanesulfonate,
1-(4-n-butoxynaphthalen-1-yl)tetrahydrothiophenium 2-(6-t-buthoxycarbonyloxybicyclo[2.2.1]heptan-2-yl)-1,1,2,2-tetrafluoroethanesulfonate,
1-(4-n-butoxynaphthalen-1-yl)tetrahydrothiophenium 1,1-difluoro-2-(bicyclo[2.2.1]heptan-2-yl)ethanesulfonate,
N-(trifluoromethanesulfonyloxy)succinimide, N-(10-camphorsulfonyloxy)succinimide,
n-[(5-methyl-5-carboxymethylbicyclo[2.2.1]heptan-2-yl)sulfonyloxy]succinimide,
N-(trifluoromethanesulfonyloxy)bicyclo[2.2.1]hept-5-ene-2,3-dicarboxylmide,
N-(nonafluoro-n-butanesulfonyloxy)bicyclo[2.2.1]hept-5-ene-2,3-dicarboxylmide,
N-[1,1,2,2-tetrafluoro-2-(norbornan-2-yl)ethanesulfonyloxy]bicyclo[2.2.1]hept-5-ene-2,3-dicarboxylmide,
N-(10-camphorsulfonyloxy)bicyclo[2.2.1]hept-5-ene-2,3-dicarboxylmide,
N-[2-(5-oxobicyclo[2.2.1]heptan-2-yl)-1,1,2,2-tetrafluoroethanesulfonyloxy]bicyclo[2.2.1]hept-5-ene-2,3-dicarboxylmide,
N-[2-(6-oxobicyclo[2.2.1]heptan-2-yl)-1,1,2,2-tetrafluoroethanesulfonyloxy]bicyclo[2.2.1]hept-5-ene-2,3-dicarboxylmide,
N-[1,1-difluoro-2-(bicyclo[2.2.1]heptan-2-yl)ethanesulfonyloxy]bicyclo[2.2.1]hept-5-ene-2,3-dicarboxylmide, bis(cyclohexanesulfonyl)diazomethane, bis(t-butylsulfonyl)diazomethane, bis(1,4-dioxaspiro[4.5]decane-7-sulfonyl)diazomethane, and the like.

The amount of the additional acid generator may be appropriately determined depending on the type of additional acid generator. The additional acid generator is normally used in an amount of 95 parts by mass or less, preferably 90 parts by mass or less, and more preferably 80 parts by mass or less, based on 100 parts by mass of the acid generator (I) and the additional acid generator in total. If the amount of the additional acid generator is more than 95 parts by mass, the desired effects of the embodiment of the present invention may be impaired.

Acid-Dissociable Group-Containing Resin

The positive-tone radiation-sensitive resin composition according to one embodiment of the present invention includes an acid-dissociable group-containing resin that is insoluble or scarcely soluble in alkali, but becomes readily soluble in alkali when the acid-dissociable group dissociates (hereinafter referred to as "acid-dissociable group-containing resin"). The expression "insoluble or scarcely soluble in alkali" means that a film that is formed only of the acid-dissociable group-containing resin has a thickness equal to or more than 50% of the initial thickness when developed under alkaline development conditions employed when forming a resist pattern using a resist film that is formed of a radiation-sensitive resin composition that includes the acid-dissociable group-containing resin.

The acid-dissociable group contained in the acid-dissociable group-containing resin refers to a group that substitutes a hydrogen atom of an acidic functional group (e.g., phenolic hydroxyl group, carboxyl group, or sulfonic acid group), and dissociates in the presence of an acid. Examples of the acid-dissociable group include a substituted methyl group, a 1-substituted ethyl group, a 1-substituted n-propyl group, a 1-branched alkyl group, an alkoxycarbonyl group, an acyl group, a cyclic acid-dissociable group, and the like.

Examples of the substituted methyl group include a methoxymethyl group, a methylthiomethyl group, an ethoxymethyl group, an ethylthiomethyl group, a (2-methoxyethoxy)methyl group, a benzyloxymethyl group, a benzylthiomethyl group, a phenacyl group, a 4-bromophenacyl group, a 4-methoxyphenacyl group, a 4-methylthiophenacyl group, an α-methylphenacyl group, a cyclopropylmethyl group, a benzyl group, a diphenylmethyl group, a triphenylmethyl group, a 4-bromobenzyl group, a 4-nitrobenzyl group, a 4-methoxybenzyl group, a 4-methylthiobenzyl group, a 4-ethoxybenzyl group, a 4-ethylthiobenzyl group, a piperonyl group, a methoxycarbonylmethyl group, an ethoxycarbonylmethyl group, an n-propoxycarbonylmethyl group, an i-propoxycarbonylmethyl group, an n-butoxycarbonylmethyl group, a t-butoxycarbonylmethyl group, and the like.

Examples of the 1-substituted ethyl group include a 1-methoxyethyl group, a 1-methylthioethyl group, a 1,1-dimethoxyethyl group, a 1-ethoxyethyl group, a 1-ethylthioethyl group, a 1,1-diethoxyethyl group, a 1-phenoxyethyl group, a 1-phenylthioethyl group, a 1,1-diphenoxyethyl group, a 1-benzyloxyethyl group, a 1-benzylthioethyl group, a 1-cyclopropyloxyethyl group, a 1-cyclohexyloxyethyl group, a 1-phenylethyl group, a 1,1-diphenylethyl group, a 1-methoxycarbonylethyl group, a 1-ethoxycarbonylethyl group, a 1-n-propoxycarbonylethyl group, a 1-i-propoxycarbonylethyl group, a 1-n-butoxycarbonylethyl group, a 1-t-butoxycarbonylethyl group, and the like.

Examples of the 1-substituted n-propyl group include a 1-methoxy-n-propyl group, a 1-ethoxy-n-propyl group, and the like. Examples of the 1-branched alkyl group include an i-propyl group, a 1-methylpropyl group, a t-butyl group, a 1,1-dimethylpropyl group, a 1-methylbutyl group, a 1,1-dimethylbutyl group, and the like. Examples of the alkoxycarbonyl group include a methoxycarbonyl group, an ethoxycarbonyl group, an i-propoxycarbonyl group, a t-butoxycarbonyl group, and the like.

Examples of the acyl group include an acetyl group, a propionyl group, a butyryl group, a heptanoyl group, a hexanoyl group, a valeryl group, a pivaloyl group, an isovaleryl group, a lauryloyl group, a myristoyl group, a palmitoyl group, a stearoyl group, an oxalyl group, a malonyl group, a succinyl group, a glutaryl group, an adipoyl group, a piperoyl group, a suberoyl group, an azelaoyl group, a sebacoyl group, an acryloyl group, a propioloyl group, a methacryloyl group, a crotonoyl group, an oleoyl group, a maleoyl group, a fumaroyl group, a mesaconoyl group, a campholoyl group, a benzoyl group, a phthaloyl group, an isophthaloyl group, a terephthaloyl group, a naphthoyl group, a toluoyl group, a hydroatropoyl group, an atropoyl group, a cinnamoyl group, a furoyl group, a thenoyl group, a nicotinoyl group, an isonicotinoyl group, a p-toluenesulfonyl group, a mesyl group, and the like.

Examples of the cyclic acid-dissociable group include a cyclopropyl group, a cyclopentyl group, a cyclohexyl group, a cyclohexenyl group, a 4-methoxycyclohexyl group, a tetrahydropyranyl group, a tetrahydrofuranyl group, a tetrahydrothiopyranyl group, a tetrahydrothiofuranyl group, a 3-bromotetrahydropyranyl group, a 4-methoxytetrahydropyranyl group, a 4-methoxytetrahydrothiopyranyl group, a 3-tetrahydrothiophene-1,1-dioxide group, and the like.

Among these acid-dissociable groups, a benzyl group, a t-butoxycarbonylmethyl group, a 1-methoxyethyl group, a 1-ethoxyethyl group, a 1-cyclohexyloxyethyl group, a 1-ethoxy-n-propyl group, a t-butyl group, a 1,1-dimethylpropyl group, a t-butoxycarbonyl group, a tetrahydropyranyl group, a tetrahydrofuranyl group, a tetrahydrothiopyranyl group, a tetrahydrothiofuranyl group, and the like are preferable. The acid-dissociable group-containing resin may include one or more types of acid-dissociable groups.

The content of the acid-dissociable groups in the acid-dissociable group-containing resin (i.e., the ratio of the number of acid-dissociable groups to the total number of acidic functional groups and acid-dissociable groups in the acid-dissociable group-containing resin) may be appropriately selected depending on the type of acid-dissociable group and the type of resin into which the acid-dissociable group is introduced, but is preferably 5 to 100%, and more preferably 10 to 100%.

The structure of the acid-dissociable group-containing resin is not particularly limited insofar as the acid-dissociable group-containing resin has the above properties. It is preferable that the acid-dissociable group-containing resin be a resin obtained by substituting some or all of the hydrogen atoms of the phenolic hydroxyl groups of poly(4-hydroxystyrene) with the acid-dissociable group, a resin obtained by substituting some or all of the hydrogen atoms of the phenolic hydroxyl groups and/or the carboxyl groups of a copolymer of 4-hydroxystyrene and/or 4-hydroxy-α-methylstyrene and (meth)acrylic acid with the acid-dissociable group, or the like.

The structure of the acid-dissociable group-containing resin may be appropriately selected depending on the type of radiation used. For example, a resin that is insoluble or scarcely soluble in alkali and includes a repeating unit shown by the following general formula (10) (hereinafter referred to as "repeating unit (10)") and a repeating unit obtained by protecting the phenolic hydroxyl group of the repeating unit (10) with the acid-dissociable group is suitably used for a positive-tone radiation-sensitive resin composition that utilizes a KrF excimer laser. Note that this resin may also be suitably used for a positive-tone radiation-sensitive resin composition that utilizes an ArF excimer laser, an F2 excimer laser, electron beams, or the like.

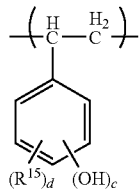

(10)

wherein $R^{15}$ represents a hydrogen atom or a monovalent organic group, and c and d represent an integer from 1 to 3.

The repeating unit (10) is preferably a unit in which the non-aromatic double bond of 4-hydroxystyrene is cleaved. The above resin may further include an additional repeating unit.

Examples of the additional repeating unit include a unit obtained by cleavage of the polymerizable unsaturated bond of a vinyl aromatic compound (e.g., styrene or α-methylstyrene), a (meth)acrylate (e.g., t-butyl(meth)acrylate, adamantyl(meth)acrylate, or 2-methyladamantyl(meth)acrylate), or the like.

A resin that is insoluble or scarcely soluble in alkali and includes a repeating unit shown by the following general formula (11) (hereinafter referred to as "repeating unit (11)") and/or a repeating unit shown by the following general formula (12) (hereinafter referred to as "repeating unit (12)"), and a repeating unit shown by the following general formula (13) (hereinafter referred to as "repeating unit (13)") is suitably used for a positive-tone radiation-sensitive resin composition that utilizes an ArF excimer laser, for example. Note that this resin may also be suitably used for a positive-tone radiation-sensitive resin composition that utilizes a KrF excimer laser, an F2 excimer laser, electron beams, or the like.

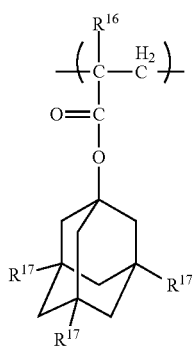

(11)

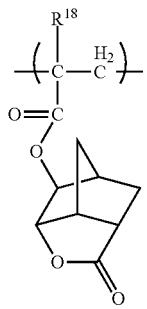

(12)

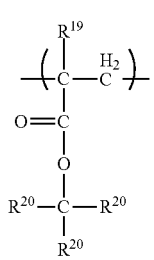

(13)

wherein $R^{16}$, $R^{18}$, and $R^{19}$ individually represent a hydrogen atom or a methyl group, R17 represents a hydrogen atom, a hydroxyl group, a cyano group, or —COOR$^{21}$ (wherein R21 represents a hydrogen atom, a linear or branched alkyl group having 1 to 4 carbon atoms, or a cycloalkyl group having 3 to 20 carbon atoms), and $R^{20}$ represents a monovalent alicyclic hydrocarbon group having 4 to 20 carbon atoms, a derivative thereof, or a linear or branched alkyl group having 1 to 4 carbon atoms, provided that at least one $R^{20}$ is the alicyclic hydrocarbon group or a derivative thereof, or two $R^{20}$ bond to form a divalent alicyclic hydrocarbon group having 4 to 20 carbon atoms or a derivative thereof together with the carbon atom that is bonded to the two $R^{20}$, and the remaining $R^{20}$ is a linear or branched alkyl group having 1 to 4 carbon atoms, a monovalent alicyclic hydrocarbon group having 4 to 20 carbon atoms, or a derivative thereof Examples of a preferable repeating unit (11) include 3-hydroxyadamantan-1-yl (meth)acrylate, 3,5-dihydroxyadamantan-1-yl(meth)acrylate, 3-cyanoadamantan-1-yl(meth)acrylate, 3-carboxyladamantan-1-yl(meth)acrylate, 3,5-dicarboxyadamantan-1-yl (meth)acrylate, 3-carboxy-5-hydroxyadamantan-1-yl(meth)acrylate, 3-methoxycarbonyl-5-hydroxyadamantan-1-yl(meth)acrylate, and the like.

Examples of a preferable repeating unit (13) include 1-methylcyclopentyl (meth)acrylate, 1-ethylcyclopentyl(meth)acrylate, 1-methylcyclohexyl(meth)acrylate, 1-ethylcyclohexyl(meth)acrylate, 2-methyladamantan-2-yl(meth)acrylate, 2-ethyladamantan-2-yl(meth)acrylate, 2-n-propyladamantan-2-yl(meth)acrylate, 2-i-propyladamantan-2-yl(meth)acrylate, 1-(adamantan-1-yl)-1-methylethyl (meth)acrylate, and the like.

The above resin may further include an additional repeating unit. Examples of the additional repeating unit include (meth)acrylates such as 7-oxo-6-oxabicyclo[3.2.1]octan-4-yl (meth)acrylate, 2-oxotetrahydropyran-4-yl (meth)acrylate, 4-methyl-2-oxotetrahydropyran-4-yl(meth)acrylate, 5-oxotetrahydrofuran-3-yl(meth)acrylate, 2-oxotetrahydrofuran-3-yl(meth)acrylate, (5-oxotetrahydrofuran-2-yl)methyl (meth)acrylate, and (3,3-dimethyl-5-oxotetrahydrofuran-2-yl)methyl(meth)acrylate; unsaturated amide compounds such as (meth)acrylamide, N,N-dimethyl(meth)acrylamide, crotonamide, maleinamide, fumaramide, mesaconamide, citraconamide, and itaconamide; unsaturated polycarboxylic anhydrides such as maleic anhydride and itaconic anhydride; bicycle[2.2.1]hept-2-ene and a derivative thereof; monofunctional monomers such as tetracyclo[6.2.1$^{3,6}$.0$^{2,7}$]dodec-3-ene and a derivative thereof; and polyfunctional monomers such as methylene glycol di(meth)acrylate, ethylene glycol di(meth)acrylate, 2,5-dimethyl-2,5-hexanediol di(meth)acrylate, 1,2-adamantanediol di(meth)acrylate, 1,3-adamantanediol di(meth)acrylate, 1,4-adamantanediol di(meth)acrylate, and tricyclodecanedimethylol di(meth)acrylate.

A polysiloxane that is insoluble or scarcely soluble in alkali and includes a structural unit shown by the following general formula (14) (hereinafter referred to as "structural unit (14)") and/or a structural unit shown by the following general formula (15) (hereinafter referred to as "structural unit (15)") is suitably used for a positive-tone radiation-sensitive resin composition that utilizes an F2 excimer laser. Note that this resin may also be suitably used for a positive-tone radiation-sensitive resin composition that utilizes a KrF excimer laser, an ArF excimer laser, electron beams, or the like.

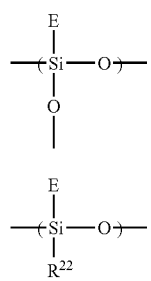

(14)

(15)

wherein E represents a monovalent organic group having an acid-dissociable group, and R$^{22}$ represents a substituted or unsubstituted, linear, branched, or cyclic monovalent hydrocarbon group having 1 to 20 carbon atoms.

The monovalent organic group represented by E in the general formulas (14) and (15) is preferably an alicyclic hydrocarbon group (e.g., cycloalkyl group, norbornyl group, tricyclodecanyl group, tetracyclodecanyl group, or adamantyl group) having an acid-dissociable group, a halogenated aromatic hydrocarbon group having an acid-dissociable group, or the like.

Examples of a preferable structural unit (14) include structural units shown by the following formulas (14-1) to (14-4) and the like.

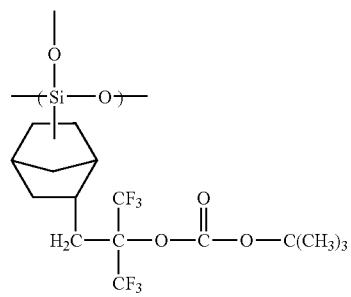

(14-1)

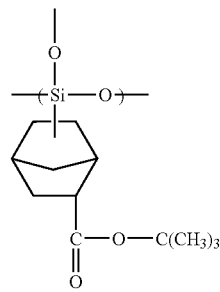

(14-2)

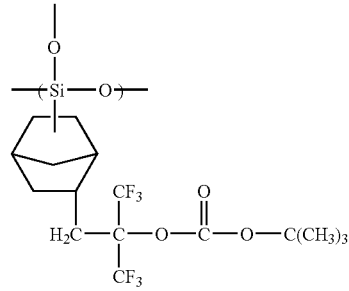

(14-3)

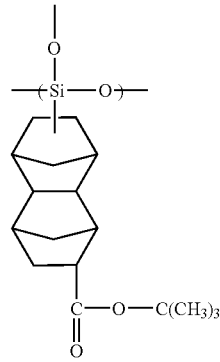

(14-4)

The above resin may further include a structural unit (hereinafter referred to as "additional structural unit") other than the above structural units. Examples of a preferable additional structural unit include a structural unit produced by hydrolysis and condensation of an alkylalkoxysilane (e.g., methyltrimethoxysilane, methyltriethoxysilane, ethyltrimethoxysilane, or ethyltriethoxysilane), structural units shown by the following formulas (16-1) to (16-4), and the like.

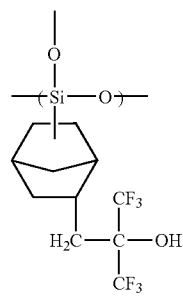

(16-1)

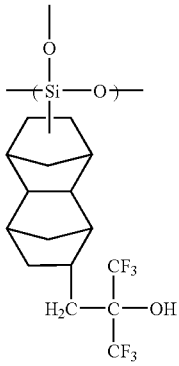

(16-2)

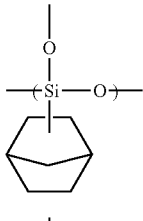

(16-3)

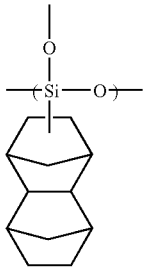

(16-4)

The above resin may be produced by (co)polycondensing at least one silane compound having an acid-dissociable group, or introducing at least one acid-dissociable group into an organic polysiloxane synthesized in advance.

It is preferable to use an acidic catalyst when (co)polycondensing the silane compound having an acid-dissociable group. It is preferable that the silane compound be polycondensed in the presence of an acidic catalyst, and further reacted after the addition of a basic catalyst.

Examples of the acidic catalyst include inorganic acids such as hydrochloric acid, sulfuric acid, nitric acid, boric acid, phosphoric acid, titanium tetrachloride, zinc chloride, and aluminum chloride; and organic acids such as formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzenesulfonic acid, p-toluenesulfonic acid, and methanesulfonic acid. Among these, hydrochloric acid, sulfuric acid, acetic acid, oxalic acid, malonic acid, maleic acid, fumaric acid, acetic anhydride, maleic anhydride, and the like are preferable.

Examples of the basic catalyst include inorganic bases such as lithium hydroxide, sodium hydroxide, potassium hydroxide, calcium hydroxide, barium hydroxide, sodium hydrogen carbonate, potassium hydrogen carbonate, sodium carbonate, and potassium carbonate, and organic bases such as triethylamine, tri-n-propylamine, tri-n-butylamine, and pyridine.

When producing the acid-dissociable group-containing resin by polymerizing a polymerizable unsaturated monomer, a branch structure may be introduced into the acid-dissociable group-containing resin using a unit derived from a polyfunctional monomer having two or more polymerizable unsaturated bonds and/or an acetal crosslinking group. The heat resistance of the acid-dissociable group-containing resin can be improved by introducing the branch structure into the acid-dissociable group-containing resin.

The content of the branch structure in the acid-dissociable group-containing resin may be appropriately selected depending on the type of branch structure and the type of resin into which the branch structure is introduced, but is preferably 10 mol % or less.

The molecular weight of the acid-dissociable group-containing resin is not particularly limited. The polystyrene-reduced weight average molecular weight (Mw) of the acid-dissociable group-containing resin determined by gel permeation chromatography (GPC) is normally 1000 to 500,000, preferably 2000 to 400,000, and more preferably 3000 to 300,000.

The Mw of the acid-dissociable group-containing resin that does not have a branch structure is preferably 1000 to 150,000, and more preferably 3000 to 100,000. The Mw of the acid-dissociable group-containing resin that has a branch structure is preferably 5000 to 500,000, and particularly preferably 8000 to 300,000. A resist obtained using the acid-dissociable group-containing resin having an Mw within the above range exhibits excellent alkali developability.

The ratio (Mw/Mn) of the Mw to the polystyrene-reduced number molecular weight (Mn) of the acid-dissociable group-containing resin determined by GPC is not particularly limited, but is normally 1 to 10, preferably 1 to 8, and more preferably 1 to 5. A resist obtained using the acid-dissociable group-containing resin having an Mw/Mn ratio within the above range exhibits excellent resolution. In the radiation-sensitive resin composition according to one embodiment of the present invention, the acid-dissociable group-containing resins may be used either individually or in combination.

The acid-dissociable group-containing resin may be produced by an arbitrary method. For example, the acid-dissociable group-containing resin may be produced by introducing one or more acid-dissociable groups into an acidic functional group of an alkali-soluble resin produced in advance, or polymerizing one or more polymerizable unsaturated monomers having an acid-dissociable group optionally together with one or more additional polymerizable unsaturated monomers, or polycondensing one or more polycondensable components having an acid-dissociable group optionally together with additional polycondensable components.

The polymerizable unsaturated monomers and the polymerizable unsaturated monomers having an acid-dissociable group may be polymerized by bulk polymerization, solution polymerization, precipitation polymerization, emulsion polymerization, suspension polymerization, bulk-suspension polymerization, or the like using an appropriate polymerization initiator (e.g., radical initiator) or an appropriate polymerization catalyst (e.g., anionic polymerization catalyst, coordination anionic polymerization catalyst, or cationic polymerization catalyst) depending on the type of polymerizable unsaturated monomer or reaction medium, for example.

The polycondensable components having an acid-dissociable group may preferably be polycondensed in an aqueous medium or a mixture of water and a hydrophilic solvent in the presence of an acidic catalyst.

The amount of the radiation-sensitive acid generator used in the positive-tone radiation-sensitive resin composition according to one embodiment of the present invention may be appropriately selected depending on the desired properties of the resist. The radiation-sensitive acid generator is preferably used in an amount of 0.001 to 70 parts by mass, more preferably 0.01 to 50 parts by mass, and particularly preferably 0.1 to 20 parts by mass, based on 100 parts by mass of the acid-dissociable group-containing resin. If the amount of the radiation-sensitive acid generator is 0.001 parts by mass or more, a decrease in sensitivity and resolution can be suppressed. If the amount of the radiation-sensitive acid generator is 70 parts by mass or less, a deterioration in resist applicability or pattern shape can be suppressed.

Alkali-Soluble Resin

The negative-tone radiation-sensitive resin composition according to one embodiment of the present invention may include an alkali-soluble resin that includes one or more functional groups that exhibit affinity with an alkaline developer, such as an oxygen-containing functional group (e.g., phenolic hydroxyl group, alcoholic hydroxyl group, or carboxyl group).

Examples of the alkali-soluble resin include an addition polymer resin that includes at least one repeating unit selected from the group consisting of a repeating unit shown by the following general formula (17) (hereinafter referred to as "repeating unit (17)"), a repeating unit shown by the following general formula (18) (hereinafter referred to as "repeating unit (18)"), and a repeating unit shown by the following general formula (19) (hereinafter referred to as "repeating unit (19)").

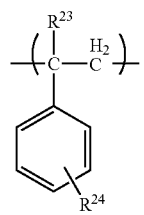

(17)

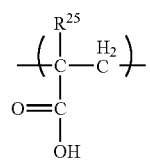

(18)

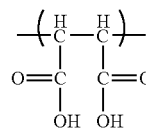

(19)

wherein $R^{23}$ and $R^{25}$ individually represent a hydrogen atom or a methyl group, and $R^{24}$ represents a hydroxyl group, a carboxyl group, $-R^{26}COOH$, $-OR^{26}COOH$, $-OCOR^{26}COOH$, or $-COOR^{26}COOH$ (wherein $R^{26}$ represents $-(CH_2)_e-$ (wherein e represents an integer from 1 to 4)).

The alkali-soluble resin may include only the repeating unit (17), (18), or (19), or may further include one or more additional repeating units insofar as the resulting resin is soluble in an alkali developer. Examples of the additional repeating units include the additional repeating units mentioned for the acid-dissociable group-containing resin.

The total content of the repeating units (17), (18), and (19) in the alkali-soluble resin varies depending on the type of additional repeating unit, but is preferably 10 to 100 mol %, and more preferably 20 to 100 mol %.

The alkali-soluble resin may be hydrogenated when the alkali-soluble resin includes a repeating unit having a carbon-carbon unsaturated bond (e.g., repeating unit (17)). In this case, the hydrogenation rate is normally 70% or less, preferably 50% or less, and more preferably 40% or less with respect to carbon-carbon unsaturated bonds contained in the repeating unit. If the hydrogenation rate is more than 70%, the alkali developability of the alkali-soluble resin may decrease.

The alkali-soluble resin preferably includes poly(4-hydroxystyrene), a 4-hydroxystyrene/4-hydroxy-α-methylstyrene copolymer, a 4-hydroxystyrene/styrene copolymer, or the like as the main component.

The Mw of the alkali-soluble resin is adjusted depending on the desired properties of the negative-tone radiation-sensitive resin composition, but is normally 1000 to 150,000, and preferably 3000 to 100,000.

In the negative-tone radiation-sensitive resin composition according to one embodiment of the present invention, the alkali-soluble resins may be used either individually or in combination.

Crosslinking Agent

The negative-tone radiation-sensitive resin composition according to one embodiment of the present invention may include a compound (hereinafter referred to as "crosslinking agent") that crosslinks the alkali-soluble resin in the presence of an acid. Examples of the crosslinking agent include a compound that includes at least one functional group (hereinafter referred to as "crosslinkable functional group") that has crosslinking reactivity with the alkali-soluble resin.

Examples of the crosslinkable functional group include a glycidyl ether group, a glycidyl ester group, a glycidylamino group, a methoxymethyl group, an ethoxymethyl group, a benzyloxymethyl group, an acetoxymethyl group, a benzoyloxymethyl group, a formyl group, an acetyl group, a vinyl group, an isopropenyl group, a (dimethylamino)methyl group, a (diethylamino)methyl group, a (dimethylolamino)methyl group, a (diethylolamino)methyl group, a morpholinomethyl group, and the like.

Examples of the crosslinking agent include a bisphenol A epoxy compound, a bisphenol F epoxy compound, a bisphenol S epoxy compound, a novolac resin epoxy compound, a resol resin epoxy compound, a poly(hydroxystyrene)epoxy compound, a methylol group-containing melamine compound, a methylol group-containing benzoguanamine compound, a methylol group-containing urea compound, a methylol group-containing phenol compound, an alkoxyalkyl group-containing melamine compound, an alkoxyalkyl group-containing benzoguanamine compound, an alkoxyalkyl group-containing urea compound, an alkoxyalkyl group-containing phenol compound, a carboxymethyl group-containing melamine resin, a carboxymethyl group-containing benzoguanamine resin, a carboxymethyl group-containing urea resin, a carboxymethyl group-containing phenol resin, a carboxymethyl group-containing melamine compound, a carboxymethyl group-containing benzoquanamine compound, a carboxymethyl group-containing urea compound, a carboxymethyl group-containing phenol compound, and the like.

Among these, a methylol group-containing phenol compound, a methoxymethyl group-containing melamine compound, a methoxymethyl group-containing phenol compound, a methoxymethyl group-containing glycoluril compound, a methoxymethyl group-containing urea compound, and an acetoxymethyl group-containing phenol compound are preferable, with a methoxymethyl group-containing melamine compound (e.g., hexamethoxymethylmelamine), a methoxymethyl group-containing glycoluril compound, a methoxymethyl group-containing urea compound, and the like being more preferable. A methoxymethyl group-containing melamine compound is commercially available as CYMEL 300, CYMEL 301, CYMEL 303, CYMEL 305 (manufactured by Mitsui Cyanamid Co., Ltd.), etc. A methoxymethyl group-containing glycoluril compound is commercially available as CYMEL 1174 (manufactured by Mitsui Cyanamid Co., Ltd.), etc. A methoxymethyl group-containing urea compound is commercially available as MX290 (manufactured by Sanwa Chemical Co., Ltd.), etc.

A resin obtained by substituting the hydrogen atom of the oxygen-containing functional group of the alkali-soluble resin with the crosslinkable functional group may also be suitably used as the crosslinking agent. The content of the crosslinkable functional group in the resin varies depending on the type of crosslinkable functional group and the type of alkali-soluble resin into which the crosslinkable functional group is introduced, but is normally 5 to 60 mol %, preferably 10 to 50 mol %, and more preferably 15 to 40 mol %, based on the total content of the oxygen-containing functional groups in the alkali-soluble resin. If the content of the crosslinkable functional group is less than 5 mol %, the film residual percentage may decrease, or the resulting pattern may be curved or may swell. If the content of the crosslinkable functional group exceeds 60 mol %, the alkali developability of the composition may decrease.

A methoxymethyl group-containing compound such as dimethoxymethylurea or tetramethoxymethylglycoluril is particularly preferable as the crosslinking agent. In the negative-tone radiation-sensitive resin composition according to one embodiment of the present invention, the crosslinking agents may be used either individually or in combination.

In the negative-tone radiation-sensitive resin composition according to one embodiment of the present invention, the radiation-sensitive acid generator is preferably used in an amount of 0.01 to 70 parts by mass, more preferably 0.1 to 50 parts by mass, and particularly preferably 0.5 to 20 parts by mass, based on 100 parts by mass of the alkali-soluble resin. If the amount of the radiation-sensitive acid generator is less than 0.01 parts by mass, the sensitivity or the resolution of the composition may decrease. If the amount of the radiation-sensitive acid generator is more than 70 parts by mass, a deterioration in resist applicability or pattern shape may occur.

The crosslinking agent is preferably used in an amount of 5 to 95 parts by mass, more preferably 15 to 85 parts by mass, and particularly preferably 20 to 75 parts by mass, based on 100 parts by mass of the alkali-soluble resin. If the amount of the crosslinking agent is less than 5 parts by mass, the film residual percentage may decrease, or the resulting pattern may be curved or may swell. If the amount of the crosslinking agent is more than 95 parts by mass, the alkali developability of the composition may decrease.

Additives

The positive-tone radiation-sensitive resin composition and the negative-tone radiation-sensitive resin composition according to one embodiment of the present invention preferably include an acid diffusion controller that controls diffusion of an acid generated by the radiation-sensitive acid generator upon exposure in a resist film to prevent undesirable chemical reactions in the unexposed area. The acid diffusion controller improves the storage stability and the resolution of the radiation-sensitive resin composition, and suppresses a change in line width of a resist pattern due to a change in post-exposure delay (PED) from exposure to development. This makes it possible to obtain a radiation-sensitive resin composition that exhibits excellent process stability.

As the acid diffusion controller, it is preferable to use a nitrogen-containing organic compound that does not change in basicity due to exposure or heating during formation of a resist pattern. Examples of the nitrogen-containing organic compound include a compound shown by the following general formula (20) (hereinafter referred to as "nitrogen-containing compound (α)"), a diamino compound that includes two nitrogen atoms in one molecule (hereinafter referred to as "nitrogen-containing compound (β)"), a polyamino compound or a polymer that includes three or more nitrogen atoms (hereinafter referred to as "nitrogen-containing compound (γ)"), an amide group-containing compound, a urea compound, a nitrogen-containing heterocyclic compound, and the like.

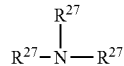

(20)

wherein $R^{27}$ represents a hydrogen atom, a substituted or unsubstituted alkyl group, a substituted or unsubstituted aryl group, or a substituted or unsubstituted aralkyl group.

Examples of the substituted or unsubstituted alkyl group represented by $R^{27}$ in the formula (20) include alkyl groups having 1 to 15, and preferably 1 to 10 carbon atoms, such as a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, an n-ethylhexyl group, an n-nonyl group, n-decyl group, a hydroxymethyl group, a 2-hydroxyethyl group, and a 3-hydroxypropyl group.

Examples of the substituted or unsubstituted aryl group represented by $R^{27}$ include aryl groups having 6 to 12 carbon atoms, such as a phenyl group, an o-tolyl group, an m-tolyl group, a p-tolyl group, a 2,3-xylyl group, a 2,4-xylyl group, a 2,5-xylyl group, a 2,6-xylyl group, a 3,4-xylyl group, a 3,5-xylyl group, a cumenyl group, and a 1-naphthyl group. Examples of the substituted or unsubstituted aralkyl group represented by $R^{27}$ include aralkyl groups having 7 to 19, and preferably 7 to 13 carbon atoms, such as a benzyl group, an α-methylbenzyl group, a phenethyl group, and a 1-naphthylmethyl group.

Examples of the nitrogen-containing compound (α) include monoalkylamines such as n-hexylamine, n-heptylamine, n-octylamine, n-nonylamine, and n-decylamine; dialkylamines such as di-n-butylamine, di-n-pentylamine, di-n-hexylamine, di-n-heptylamine, di-n-octylamine, di-n-nonylamine, and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, and tri-n-decylamine; alkanolamines such as ethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine; and the like.

Examples of the nitrogen-containing compound (β) include ethylenediamine, N,N,N',N'-tetramethylethylenediamine, tetramethylenediamine, hexamethylenediamine, N,N,N',N'-tetrakis(2-hydroxyethyl)ethylenediamine, N,N,N',N'-tetrakis(2-hydroxypropyl)ethylenediamine, 4,4'-diaminodiphenylmethane, 4,4'-diamino diphenyl ether, 4,4'- diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, and the like. Examples of the nitrogen-containing compounds (γ) include polyethyleneimine, polyallylamine, poly(N-(2-dimethylaminoethyl)acrylamide), and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles such as imidazole, benzimidazole, 2-methylimidazole, 4-methylimidazole, 1,2-dimethylimidazole, 2-phenylimidazole, 4-phenylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, N-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, 1-piperidine ethanol, 2-piperidine ethanol, morpholine, 4-methylmorpholine, piperazine, 1,4-dimethylpiperazine, 1,4-diazabicyclo[2.2.2]octane, and the like.

A compound having an acid-dissociable group may also be used as the nitrogen-containing organic compound. Examples of the nitrogen-containing organic compound having an acid-dissociable group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, tert-butyl 4-hydroxy-1-piperidinecarboxylate, and the like.

Among these nitrogen-containing organic compounds, the nitrogen-containing compound (α), the nitrogen-containing compounds (β), the nitrogen-containing heterocyclic compound, the nitrogen-containing organic compound having an acid-dissociable group, and the like are preferable. The acid diffusion controllers may be used either individually or in combination.

The acid diffusion controller is preferably used in an amount of 15 parts by mass or less, more preferably 0.001 to 10 parts by mass, and particularly preferably 0.005 to 5 parts by mass, based on 100 parts by mass of the acid-dissociable group-containing resin or the alkali-soluble resin. If the amount of the acid diffusion controller is 0.001 parts by mass or more, a deterioration in pattern shape or dimensional accuracy due to process conditions can be suppressed. If the amount of the acid diffusion controller is 15 parts by mass or less, the sensitivity and the alkali developability of the resulting resist can be improved.

The positive-tone radiation-sensitive resin composition and the negative-tone radiation-sensitive resin composition according to one embodiment of the present invention may include a dissolution controller that improves solubility in an alkaline developer due to an acid.

Examples of the dissolution controller include a compound that includes an acid functional group (e.g., phenolic hydroxyl group, carboxyl group, or sulfonic acid group), a compound obtained by substituting the hydrogen atom of the acidic functional group of the above compound with an acid-dissociable group, and the like.

The dissolution controller may be a low-molecular-weight compound or a high-molecular-weight compound. The acid-dissociable group-containing resin used for the positive-tone radiation-sensitive resin composition may be used as the high-molecular-weight dissolution controller used for the negative-tone radiation-sensitive resin composition, for example. The dissolution controllers may be used either individually or in combination.

The dissolution controller is normally used in an amount of 50 parts by mass or less, and preferably 20 parts by mass or less, based on 100 parts by mass of the resin component contained in the radiation-sensitive resin composition.

The positive-tone radiation-sensitive resin composition and the negative-tone radiation-sensitive resin composition according to one embodiment of the present invention may include a surfactant that improves the applicability, striation, developability, etc. of the radiation-sensitive resin composition.

As the surfactant, an anionic surfactant, a cationic surfactant, a nonionic surfactant, or an ampholytic surfactant may be used. It is preferable to use a nonionic surfactant.

Examples of the nonionic-type surfactant include polyoxyethylene higher alkyl ethers, polyoxyethylene higher alkyl phenyl ethers, higher fatty acid diesters of polyethylene glycol, KP (manufactured by Shin-Etsu Chemical Co., Ltd.), Polyflow (manufactured by Kyoeisha Chemical Co., Ltd.), EFTOP (manufactured by Jemco Inc.), Megafac (manufactured by DIC Corporation), Fluorad (manufactured by Sumitomo 3M, Ltd.), Asahi Guard, Surflon (manufactured by Asahi Glass Co., Ltd.), and the like. These surfactants may be used either individually or in combination.

The surfactant is normally used in an amount of 2 parts by mass or less, and preferably 1.5 parts by mass or less (amount of effective component), based on 100 parts by mass of the resin component contained in the radiation-sensitive resin composition.

The positive-tone radiation-sensitive resin composition and the negative-tone radiation-sensitive resin composition according to one embodiment of the present invention may include a sensitizer that absorbs the energy of radiation and transmits the energy to the radiation-sensitive acid generator so that the amount of acid generated increases. This improves the apparent sensitivity of the radiation-sensitive resin composition. Examples of the sensitizer include acetophenones, benzophenones, naphthalenes, biacetyl, eosine, rose bengale, pyrenes, anthracenes, phenothiazines, and the like. These sensitizers may be used either individually or in combination.

The sensitizer is normally used in an amount of 50 parts by mass or less, and preferably 30 parts by mass or less, based on 100 parts by mass of the resin component contained in the radiation-sensitive resin composition.

The positive-tone radiation-sensitive resin composition and the negative-tone radiation-sensitive resin composition according to one embodiment of the present invention may include other additives such as a dye, a pigment, an adhesion improver, a halation inhibitor, a preservative, a defoaming agent, and a shape improver (e.g., 4-hydroxy-4'-methyl chalcone) insofar as the effects of the embodiment of the present invention are not impaired. A dye or a pigment visualizes the latent image of the exposed area so that the effects of halation during exposure can be reduced. An adhesion improver improves adhesion to a substrate.

Preparation of Composition Solution

The positive-tone radiation-sensitive resin composition and the negative-tone radiation-sensitive resin composition according to one embodiment of the present invention are normally prepared as a composition solution by dissolving each component in a solvent to obtain a homogeneous solution, and optionally filtering the solution through a filter having a pore size of about 0.2 μm.

Examples of the solvent include ethers, esters, ether esters, ketones, ketone esters, amides, amide esters, lactams, lactones, (halogenated) hydrocarbons, and the like. Specific examples of the solvent include ethylene glycol monoalkyl ethers, diethylene glycol dialkyl ethers, propylene glycol monoalkyl ethers, propylene glycol dialkyl ethers, ethylene glycol monoalkyl ether acetates, propylene glycol monoalkyl ether acetates, acyclic or cyclic ketones, acetates, hydroxyacetates, alkoxyacetates, acetoacetates, propionates, lactates, substituted propionates, (substituted) butylates, pyruvates, N,N-dialkylformamides, N,N-dialkylacetamides, N-alkylpyrolidones, (halogenated) aliphatic hydrocarbons, (halogenated) aromatic hydrocarbons, and the like.

More specific examples of the solvent include ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, propylene glycol monomethyl ether acetate, propylene glycol monoethyl ether acetate, propylene glycol mono-n-propyl ether acetate, methyl ethyl ketone, 2-heptanone, 3-heptanone, 4-heptanone, cyclohexanone, ethyl acetate, n-propyl acetate, n-butyl acetate, isopropenyl acetate, 3-methoxybutyl acetate, 3-methyl-3-methoxybutyl acetate, ethyl hydroxyacetate, ethyl ethoxyacetate, methyl acetoacetate, ethyl acetoacetate, isopropenyl propionate, 3-methyl-3-methoxybutyl propionate, methyl lactate, ethyl lactate, n-propyl lactate, i-propyl lactate, methyl 3-methoxypropionate, ethyl 3-methoxypropionate, methyl 3-ethoxypropionate, ethyl 3-ethoxypropionate, 3-methyl-3-methoxybutyl butyrate, methyl 2-hydroxy-3-methylbutyrate, ethyl 2-hydroxy-2-methyl propionate, N,N-dimethylformamide, N,N-dimethylacetamide, N-methylpyrolidone, toluene, xylene, and the like.

Among these, propylene glycol monoalkyl ether acetates, acyclic or cyclic ketones, lactates, 3-alkoxypropionate, and the like are preferable to achieve excellent in-plane uniformity during application. These solvents may be used either individually or in combination.

An additional solvent having a high boiling point, such as benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, or ethylene glycol monophenyl ether acetate, may optionally be used in addition to the above solvent. Among these, γ-butyrolactone is preferable.

The additional solvents may be used either individually or in combination. The additional solvent is normally used in an amount of 50 mass % or less, and preferably 30 mass % or less, based on the total amount of solvents.

The solvent is normally used so that the total solid content in the composition solution is 5 to 50 mass %, preferably 10 to 50 mass %, more preferably 10 to 40 mass %, particular preferably 10 to 30 mass %, and still more preferably 10 to 25 mass %. If the total solid content in the composition solution is within the above range, excellent in-plane uniformity can be achieved during application.

Formation of Resist Pattern

A resist pattern is formed as follows using the positive-tone radiation-sensitive resin composition or the negative-tone radiation-sensitive resin composition according to one embodiment of the present invention. Specifically, the composition solution prepared as described above is applied to a substrate (e.g., silicon wafer or aluminum-coated wafer) using an appropriate application method (e.g., rotational coating, cast coating, or roll coating) to form a resist film. After performing an optional heat treatment (hereinafter referred to as "PB"), the resist film is exposed through a mask having a given pattern.

Deep ultraviolet rays (e.g., mercury lamp line spectrum (wavelength: 254 nm), KrF excimer laser light (wavelength: 248 nm), ArF excimer laser light (wavelength: 193 nm), F2 excimer laser light (wavelength: 157 nm), and EUV light (wavelength: 13 nm)), X-rays (e.g., synchrotron radiation), charged particle rays (e.g., electron beams), or the like may be used for exposure depending on the type of radiation-sensitive acid generator. It is preferable to use deep ultraviolet rays or charged particle rays (particularly KrF excimer laser light (wavelength: 248 nm), ArF excimer laser light (wavelength: 193 nm), F2 excimer laser light (wavelength: 157 nm), or electron beams).

The exposure conditions (e.g. dose) are appropriately determined depending on the composition of the positive-tone radiation-sensitive resin composition or the negative-tone radiation-sensitive resin composition, the type of additive, and the like. It is preferable to perform post-exposure bake (PEB) after exposure in order to improve the apparent sensitivity of the resulting resist. PEB is normally performed at 30 to 200° C., and preferably 50 to 150° C., although the PEB conditions are appropriately adjusted depending on the composition of the radiation-sensitive resin composition, the type of additive, and the like.

The exposed resist film is then developed using an alkaline developer to form a positive-tone or negative-tone resist pattern.

Examples of the alkaline developer include an alkaline aqueous solution prepared by dissolving at least one alkaline compound such as an alkali metal hydroxide, aqueous ammonia, an alkylamine, an alkanolamine, a heterocyclic amine, a tetraalkylammonium hydroxide, choline, 1,8-diazabicyclo[5.4.0]-7-undecene, or 1,5-diazabicyclo[4.3.0]-5-nonene. An aqueous solution of a tetraalkylammonium hydroxide is particularly preferably used as the alkaline developer.

The concentration of the alkaline aqueous solution is preferably 10 mass % or less, more preferably 1 to 10 mass %, and particularly preferably 2 to 5 mass %. If the concentration of the alkaline aqueous solution is 10 mass % or less, dissolution of the unexposed area (positive-tone resist pattern) or the exposed area (negative-tone resist pattern) in the alkaline developer can be prevented.

It is preferable to add an appropriate amount of surfactant or the like to the alkaline aqueous solution in order to increase the wettability of the resist film with the alkaline developer. After developing the resist film using the developer (alkaline aqueous solution), the resist film is normally washed with water, and then dried.

EXAMPLES

The present invention is further described below by way of examples. Note that the present invention is not limited to the following examples.

Example 1

A compound (sodium 2-(adamantan-1-yl)-1,1-difluoroethane-1-sulfonate) shown by the following formula (21) was synthesized by the following method.

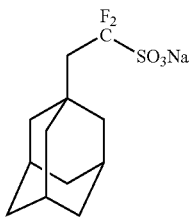
(21)

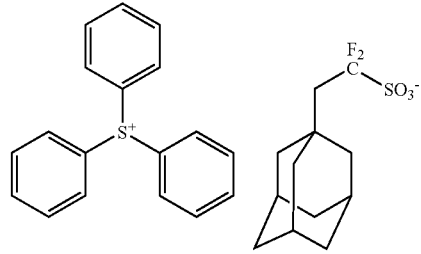
(B-a)

A reaction flask was charged with 97.5 g of sodium dithionite and 70.6 g of sodium carbonate. After the addition of 660 ml of ion-exchanged water, the mixture was stirred for 30 minutes. A solution prepared by dissolving 91.4 g of 1-(adamantan-1-yl)-2,2-difluoro-2-iodoethane in 660 ml of acetonitrile was added dropwise to the mixture over 15 minutes. The mixture was heated (internal temperature: 60° C.) for 3.5 hours with stiffing. After removing the reaction solvent under reduced pressure, the product was concentrated to dryness to obtain 362 g of sodium 2-(adamantan-1-yl)-1,1-difluoroethane-1-sulfinate as a white solid. The purity was 38.9 wt %.

A reaction flask was charged with 362 g of sodium 2-(adamantan-1-yl)-1,1-difluoroethane-1-sulfinate and 1.5 l of dichloromethane. The mixture was stirred at 0° C. After the dropwise addition of 1.5 l of 4N sulfuric acid at 0° C. over 20 minutes, the mixture was stirred at 0° C. for one hour. The dichloromethane layer was removed to obtain 76.3 g of purified sodium 2-(adamantan-1-yl)-1,1-difluoroethane-1-sulfinate as a pale red-brown solid. After the addition of 5.5 l of ion-exchanged water, 28.1 g of sodium carbonate, and 0.92 g of sodium tungstate to the pale red-brown solid, the mixture was stirred for 30 minutes. After the dropwise addition of 30 ml of a 30 wt % hydrogen peroxide solution to the reaction mixture over 30 minutes, the mixture was stirred at 60° C. for three hours. The reaction solvent was then removed under reduced pressure to obtain 87.9 g of sodium 2-(adamantan-1-yl)-1,1-difluoroethane-1-sulfonate as a white solid.

The resulting sodium 2-(adamantan-1-yl)-1,1-difluoroethane-1-sulfonate was analyzed by $^1$H-NMR ("JNM-EX270" manufactured by JEOL Ltd.). The chemical shift was $^1$H-NMR [σ ppm (D$_2$O): 1.64-1.76 (12H, m), 1.92-2.10 (5H, m)] and $^{19}$F-NMR [a ppm (DMSO): 58.82 (m)] (the peak of sodium 3-trimethylsilylpropionate-2-2,2,3,3-d$_4$ ($^1$H-NMR) or the peak of hexafluorobenzene ($^{19}$F-NMR) was determined to be 0 ppm (internal standard)). This indicates that the target compound was obtained. The purity was 93 wt % (measured by $^1$H-NMR).

Example 2

A compound (triphenylsulfonium 2-(adamantan-1-yl)-1,1-difluoroethane-1-sulfonate) shown by the following formula (B-a) was synthesized by the following method.

A reaction flask was charged with 53.2 g of sodium 2-(adamantan-1-yl)-1,1-difluoroethane-1-sulfonate and 54.9 g of triphenylsulfonium bromide. After the addition of 500 ml of ion-exchanged water and 500 ml of dichloromethane, the mixture was stirred at room temperature for one hour. The organic layer was separated, and washed five times with 500 ml of ion-exchanged water. The solvent was then removed to obtain 78.1 g of triphenylsulfonium 2-(adamantan-1-yl)-1,1-difluoroethane-1-sulfonate. The resulting triphenylsulfonium 2-(adamantan-1-yl)-1,1-difluoroethane-1-sulfonate was analyzed by $^1$H-NMR ("JNM-EX270" manufactured by JEOL Ltd.) (solvent: deuterated water). The chemical shift was $^1$H-NMR [σ ppm (D$_2$O): 1.64-1.76 (12H, m), 1.92-2.10 (5H, m), 7.76-7.89 (15H, m)] and $^{19}$F-NMR [σ ppm (DMSO-d$_6$): 58.82 (m)] (the peak of sodium 3-trimethylsilylpropionate-2-2,2,3,3-d$_4$ ($^1$H-NMR) or the peak of hexafluorobenzene ($^{19}$F-NMR) was determined to be 0 ppm). This indicates that the target compound was obtained. The purity was 99 wt % or higher.

Example 3

The following compounds were obtained in the same manner as in Example 2.

4-n-Butoxy-1-naphthyltetrahydrothiophenium 2-(adamantan-1-yl)-1,1-difluoroethane-1-sulfonate (B-b)

The NMR analysis results are as follows: $^1$H-NMR [σ ppm (CDCl$_3$): 1.04 (3H, t, J=7.36 Hz), 1.56-1.63 (5H, m), 1.64-1.76 (12H, m), 1.91-2.11 (7H, m), 2.61-2.67 (4H, m), 3.67-3.71 (2H, m), 4.22-4.31 (4H, m), 7.05 (1H, d, J=8.56 Hz), 7.65-7.80 (2H, m), 7.94 (1H, d, J=8.60 Hz), 8.26 (1H, d, J=8.56 Hz), 8.42 (1H, d, J=8.56 Hz)], $^{19}$F-NMR [σ ppm (CDCl$_3$): 58.86 (m)]. This indicates that the target compound was obtained. The purity was 99 wt % or higher.

Diphenylsulfonium 4-cyclohexylphenylsulfonium 2-(adamantan-1-yl)-1,1-difluoroethane-1-sulfonate (B-c)

The NMR analysis results are as follows: $^1$H-NMR [σ ppm (CDCl$_3$): 1.18-1.48 (5H, m), 1.63-1.95 (10H, m), 1.92-2.10 (5H, m), 2.61 (1H, m), 7.51 (2H, m), 7.65-7.77 (12H, m)], $^{19}$F-NMR [σ ppm (CDCl$_3$): δ8.91 (m)]. This indicates that the target compound was obtained. The purity was 99 wt % or higher.

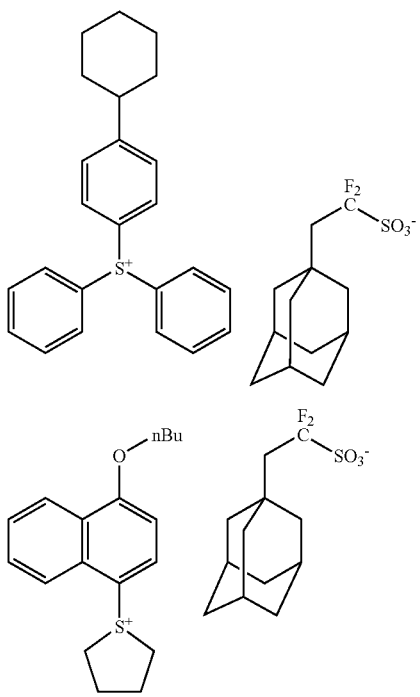

(B-b)

(B-c)

Synthesis of Resin

Example 3

A monomer solution was prepared by dissolving 21.17 g (25 mol %) of a compound (S-1), 27.21 g (25 mol %) of a compound (S-4), and 51.62 g (50 mol %) of a compound (S-5) in 200 g of 2-butanone, and adding 3.81 g of dimethyl 2,2'-azobis(2-methylpropionate) to the solution. A three-necked flask (1000 ml) charged with 100 g of 2-butanone was purged with nitrogen for 30 minutes, and then heated to 80° C. with stirring. The monomer solution was added dropwise to the flask using a dropping funnel over three hours. The monomers were polymerized for six hours in total. After completion of polymerization, the polymer solution was cooled with water to 30° C. or less, and added to 2000 g of methanol. A white powder that precipitated was filtered off. The white powder was dispersed in (washed with) 400 g of methanol, and filtered off. This operation was repeated once. The powder was then dried at 50° C. for 17 hours to obtain a white powdery copolymer (resin (A)) (74 g, yield: 74%). The copolymer had an Mw of 6180 and an Mw/Mn ratio of 1.717. As a result of $^{13}$C-NMR analysis, it was found that the ratio of repeating units derived from the compounds (S-1), (S-4), and (S-5) contained in the copolymer was 24.5:24.2:51.3 (mol %). The copolymer is referred to as "polymer (A-1)".

In the examples and comparative examples, the following properties were measured and evaluated as follows.

Sensitivity

A silicon wafer coated with an ARC29 (manufactured by Brewer Science) film (thickness: 780 angstroms) was spin-coated with the composition solution, and pre-baked (PB) on a hot plate at a temperature shown in Tables 1-1 and 1-2 for 60 minutes to obtain a resist film having a thickness of 0.12 μm. The resist film was exposed through a mask pattern using an ArF excimer laser exposure system (manufactured by Nikon Corp., numerical aperture: 0.78). After performing PEB at a temperature shown in Tables 1-1 and 1-2 for 60 seconds, the resist film was developed at 25° C. for 30 seconds using a 2.38 mass % tetramethylammonium hydroxide aqueous solution, washed with water, and dried to form a positive-tone resist pattern. The optimum dose at which a 1:1 line-and-space (1L1S) pattern having a line width of 90 nm was formed was taken as sensitivity.

Mask Linearity

A value obtained by subtracting 75 from the difference between the line width resolved at the optimum dose using an 85 nm 1L/1S mask and the line width resolved at the optimum dose using an 160 nm 1L/1S mask was taken as mask linearity.

LWR

The line width of a 90 nm 1L/1S pattern resolved at the optimum dose was observed from above at an arbitrary ten points using a scanning electron microscope (SEM) ("S9220" manufactured by Hitachi, Ltd.), and a variation (36) in line width was taken as the LWR.

MEEF

The optimum dose sensitivity was measured so that the line width of a 90 nm 1L/1S pattern was 90 nm when using a mask having a line width of 90 nm. The dimension of the pattern resolved at the optimum dose sensitivity using each mask (85.0 nm, 87.5 nm, 90.0 nm, 92 nm, and 95.0 nm) was measured. The mask size (horizontal axis) and the line width (vertical axis) were plotted on a graph, and the slope determined by the least-square method was taken as the MEEF.

100 parts of the polymer (A-1), 7.5 parts of a radiation-sensitive acid generator (acid generator) (B-1), and 0.7 parts of an acid diffusion controller (C) were mixed to obtain a radiation-sensitive resin composition. 1500 parts of a solvent (D-1), 650 parts of a solvent (D-2), and 30 parts of a solvent (D-3) were mixed to prepare a mixed solvent. The resulting radiation-sensitive resin composition was dissolved in the mixed solvent to obtain a radiation-sensitive resin composition solution. The amount of each solvent is indicated by the mass ratio (parts by mass) relative to 100 parts of the polymer (A-1). The resulting radiation-sensitive resin composition solution was subjected to the above measurements. The measurement results are shown in Tables 2-1 and 2-2.

(S-1)

(S-2)

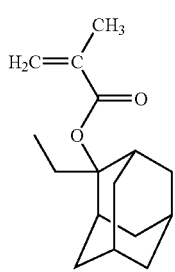 (S-3)

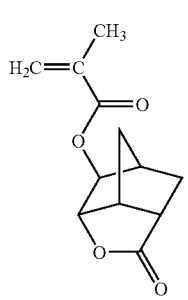 (S-5)

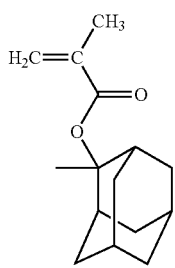 (S-4)

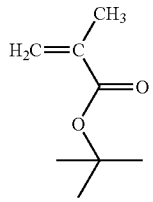 (S-6)

TABLE 1-1

|  | | Resin (parts) | Acid generator (parts) | Acid diffusion controller (parts) | Solvent (parts) |
|---|---|---|---|---|---|
| Example | 1 | A-1 (100) | B-a (8.1) | C (0.5) | D-1 (1500), D-2 (650), D-3 (30) |
|  | 2 | A-1 (100) | B-b (9.3) | C (0.5) | D-1 (1500), D-2 (650), D-3 (30) |
|  | 3 | A-1 (100) | B-a (7.1) B-c (2.0) | C (0.6) | D-1 (1500), D-2 (650), D-3 (30) |
|  | 4 | A-1 (100) | B-b (5.3) B-c (8.0) | C (0.6) | D-1 (1500), D-2 (650), D-3 (30) |
|  | 5 | A-2 (100) | B-a (8.1) | C (0.5) | D-1 (1500), D-2 (650), D-3 (30) |
|  | 6 | A-2 (100) | B-a (4.1) B-b (4.6) | C (0.6) | D-1 (1500), D-2 (650), D-3 (30) |
|  | 7 | A-3 (100) | B-a (8.1) | C (0.5) | D-1 (1500), D-2 (650), D-3 (30) |
|  | 8 | A-3 (100) | B-b (9.3) | C (0.6) | D-1 (1500), D-2 (650), D-3 (30) |
|  | 9 | A-4 (100) | B-a (8.1) | C (0.5) | D-1 (1500), D-2 (650), D-3 (30) |
|  | 10 | A-4 (100) | B-a (1.5) B-c (12.0) B-1 (13.0) | C (0.7) | D-1 (1500), D-2 (650), D-3 (30) |

TABLE 1-2

|  | | Resin (parts) | Acid generator (parts) | Acid diffusion controller (parts) | Solvent (parts) |
|---|---|---|---|---|---|
| Comparative Example | 1 | A-1 (100) | B-3 (8.4) | C (1.0) | D-1 (1500), D-2 (650), D-3 (30) |
|  | 2 | A-1 (100) | B-6 (9.6) | C (1.0) | D-1 (1500), D-2 (650), D-3 (30) |
|  | 3 | A-1 (100) | B-2 (8.0) | C (0.7) | D-1 (1500), D-2 (650), D-3 (30) |
|  | 4 | A-1 (100) | B-1 (7.5) | C (0.6) | D-1 (1500), D-2 (650), D-3 (30) |
|  | 5 | A-1 (100) | B-3 (7.4) B-5 (2.3) | C (0.6) | D-1 (1500), D-2 (650), D-3 (30) |
|  | 6 | A-1 (100) | B-2 (7.0) B-2 (2.2) | C (0.6) | D-1 (1500), D-2 (650), D-3 (30) |
|  | 7 | A-1 (100) | B-6 (5.6) B-5 (8.0) | C (1.0) | D-1 (1500), D-2 (650), D-3 (30) |
|  | 8 | A-2 (100) | B-3 (8.4) | C (1.0) | D-1 (1500), D-2 (650), D-3 (30) |
|  | 9 | A-2 (100) | B-3 (4.2) B-6 (4.7) | C (1.0) | D-1 (1500), D-2 (650), D-3 (30) |
|  | 10 | A-3 (100) | B-3 (8.4) | C (1.0) | D-1 (1500), D-2 (650), D-3 (30) |
|  | 11 | A-3 (100) | B-6 (9.6) | C (1.0) | D-1 (1500), D-2 (650), D-3 (30) |
|  | 12 | A-4 (100) | B-3 (8.4) | C (1.0) | D-1 (1500), D-2 (650), D-3 (30) |
|  | 13 | A-4 (100) | B-3 (1.6) B-1 (13.0) | C (1.0) | D-1 (1500), D-2 (650), D-3 (30) |

Radiation-Sensitive Acid Generator (B)

B-1: 1-(4-n-butoxynaphthyl)tetrahydrothiophenium nonafluoro-n-butanesulfonate

B-2: triphenylsulfonium 2-bicyclo[2.2.1]hept-2-yl-1,1,2,2-tetrafluoroethanesulfonate B-3: triphenylsulfonium perfluoro-n-butanesulfonate B-4: 4-n-butoxy-1-naphthyltetrahydrothiophenium 2-bicyclo[2.2.1]hept-2-yl-1,1,2,2-tetrafluoroethanesulfonate B-5: 4-n-butoxy-1-naphthyltetrahydrothiophenium nonafluorobutanesulfonate B-6: 4-cyclohexylphenyl-diphenylsulfonium nonafluoro-n-butanesulfonate The radiation-sensitive acid generators (B-1) to (B-6) are shown by the following formulas (B-1) to (B-6).

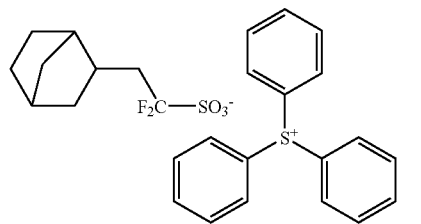
(B-1)

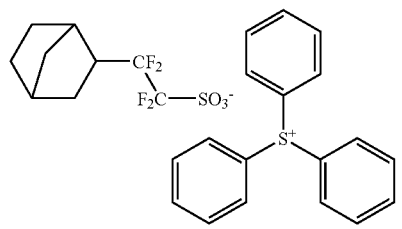
(B-2)

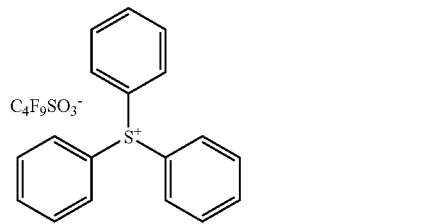
(B-3)

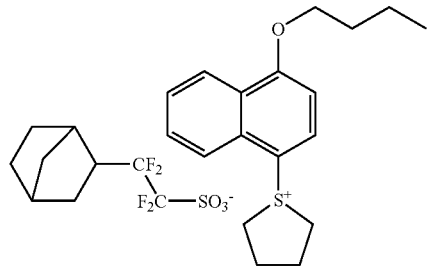
(B-4)

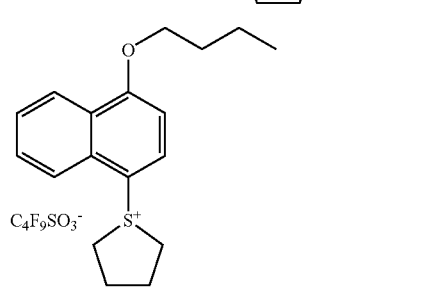
(B-5)

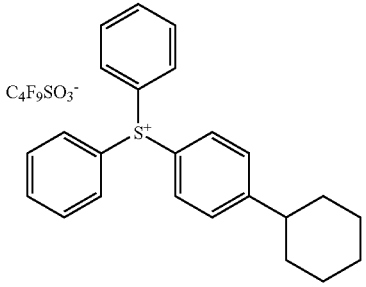
(B-6)

Acid Diffusion Controller (C)

(C): tert-butyl 4-hydroxy-1-piperidinecarboxylate

The acid diffusion controller (C) is shown by the following formula (C).

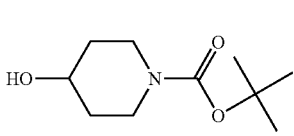
(C)

Solvent (D)

(D-1): propylene glycol monomethyl ether acetate (D-2): cyclohexanone (D-3): γ-butyrolactone The solvents (D-1) to (D-3) are shown by the following formulas (D-1) to (D-3).

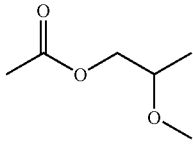
(D-1)

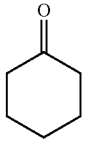
(D-2)

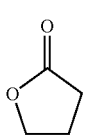
(D-3)

Radiation-sensitive resin compositions (Examples 2 to 10 and Comparative Examples 1 to 13) were produced in the same manner as in Example 1, except for producing polymers (resins (A-2) to (A-4)) in accordance with the following molar ratio (see "Copolymer (resin (A))") and mixing each of the polymers (resins (A-2) to (A-4)) with the radiation-sensitive acid generator (B) and the acid diffusion controller (C) in a ratio shown in Tables 1-1 and 1-2. The resulting radiation-sensitive resin composition was dissolved in a mixed solvent prepared by mixing the solvent (D) in a ratio shown in Tables 1-1 and 1-2 to obtain a radiation-sensitive resin composition solution. In Tables 1-1 and 1-2, the term "resin" refers to "copolymer (resin (A))". The resulting radiation-sensitive resin composition solution was subjected to the above measurements. The measurement results are shown in Tables 2-1 and 2-2.

Copolymer (Resin (A))

A-2: (S-2) 35/(S-3) 15/(S-5) 50=34.3/15.5/50.2 (molar ratio), Mw=5768, Mw/Mn=1.698

A-3: (S-1) 15/(S-4) 35/(S-5) 50=14.5/36.7/48.8 (molar ratio), Mw=6708, Mw/Mn=1.723

A-4: (S-2) 25/(S-5) 50/(S-6) 25=23.9/53.4/22.6 (molar ratio), Mw=6811, Mw/Mn=1.348

TABLE 2-1

| | | PB (° C.) | PEB (° C.) | Sensitivity (mJ/cm$^2$) | Mask linearity | LWR (nm) | MEEF |
|---|---|---|---|---|---|---|---|
| Example | 1 | 100 | 105 | 44.0 | 0.36 | 6.7 | 3.2 |
| | 2 | 100 | 105 | 46.0 | 0.38 | 6.8 | 3.0 |
| | 3 | 100 | 105 | 38.0 | 0.32 | 6.4 | 3.4 |
| | 4 | 100 | 105 | 39.0 | 0.33 | 6.5 | 3.3 |
| | 5 | 100 | 100 | 45.5 | 0.37 | 6.8 | 3.0 |
| | 6 | 100 | 100 | 46.0 | 0.38 | 6.9 | 2.9 |
| | 7 | 100 | 115 | 42.0 | 0.33 | 6.7 | 3.2 |
| | 8 | 100 | 115 | 4.4 | 0.35 | 6.8 | 3.1 |
| | 9 | 100 | 130 | 40.0 | 0.31 | 7.0 | 2.9 |
| | 10 | 100 | 130 | 38.0 | 0.29 | 6.8 | 3.2 |

TABLE 2-2

| | | PB (° C.) | PEB (° C.) | Sensitivity (mJ/cm$^2$) | Mask linearity | LWR (nm) | MEEF |
|---|---|---|---|---|---|---|---|
| Comparative Example | 1 | 100 | 105 | 38.0 | 0.13 | 8.2 | 3.8 |
| | 2 | 100 | 105 | 41.0 | 0.14 | 8.0 | 3.3 |
| | 3 | 100 | 105 | 40.0 | 0.23 | 7.6 | 3.4 |
| | 4 | 100 | 105 | 41.0 | 0.23 | 7.2 | 3.4 |
| | 5 | 100 | 105 | 37.0 | 0.10 | 7.9 | 4.2 |
| | 6 | 100 | 105 | 37.5 | 0.20 | 7.2 | 4.2 |
| | 7 | 100 | 105 | 38.0 | 0.11 | 7.4 | 4.0 |
| | 8 | 100 | 100 | 38.0 | 0.20 | 7.7 | 4.0 |
| | 9 | 100 | 100 | 40.0 | 0.18 | 7.6 | 3.8 |
| | 10 | 100 | 115 | 35.0 | 0.12 | 8.1 | 4.3 |
| | 11 | 100 | 115 | 38.0 | 0.14 | 8.0 | 4.1 |
| | 12 | 100 | 130 | 38.0 | 0.12 | 8.4 | 3.5 |
| | 13 | 100 | 130 | 40.0 | 0.09 | 8.0 | 3.9 |

The compound according to the embodiment of the present invention exhibits excellent transparency to active radiation such as deep ultraviolet rays (e.g., KrF excimer laser light, ArF excimer laser light, F2 excimer laser light, or EUV) and electron beams, generates an acid having sufficiently high acidity upon exposure to active radiation or heating, the acid having a moderately short diffusion length in a resist film and a high carbon content, and is suitably used as a radiation-sensitive acid generator for a radiation-sensitive resin composition that exhibits excellent mask linearity, MEEF, and LWR and is useful as a chemically-amplified resist.

The compound according to the embodiment of the present invention is useful as a radiation-sensitive acid generator used for a radiation-sensitive resin composition that is useful as a chemically-amplified resist.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A radiation-sensitive resin composition comprising:
a compound comprising a partial structure shown by a following formula (1),

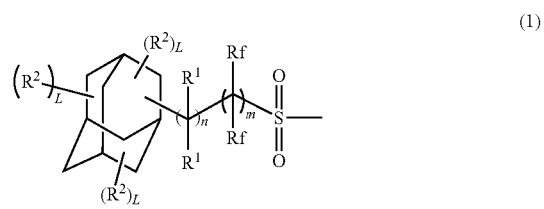

wherein R$^1$ represents a hydrogen atom or a substituted or unsubstituted hydrocarbon group having 1 to 8 carbon atoms, R$^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents 1, and m represents 1; and an acid-dissociable group-containing resin, wherein the resin comprises at least:

(a) a resin that is insoluble or scarcely soluble in alkali and includes a repeating unit (10) shown by the following general formula (10) and a repeating unit obtained by protecting the phenolic hydroxyl group of repeating unit (10) with the acid-dissociable group

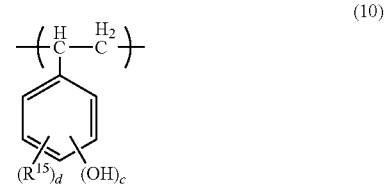

wherein R$^{15}$ represents a hydrogen atom or a monovalent organic group, and c and d represent an integer from 1 to 3; or (b) a resin that is insoluble or scarcely soluble in alkali and includes a repeating unit shown by the following general formula (13),

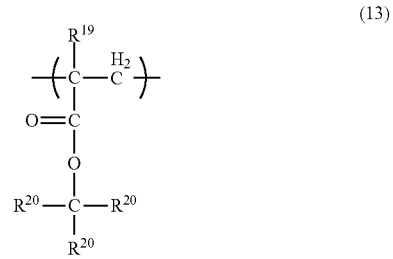

wherein R$^{19}$ represents a hydrogen atom or a methyl group, and R$^{20}$ represents a monovalent alicyclic hydrocarbon group having 4 to 20 carbon atoms, a derivative thereof, or a linear or branched alkyl group having 1 to 4 carbon atoms, provided that at least one R$^{20}$ is the alicyclic hydrocarbon group or a derivative thereof, or two R$^{20}$ bond to form a divalent alicyclic hydrocarbon group having 4 to 20 carbon atoms or a derivative thereof together with the carbon atom that is bonded to the two R$^{20}$, and the remaining R$^{20}$ is a linear or branched alkyl group having 1 to 4 carbon atoms, a monovalent alicyclic hydrocarbon group having 4 to 20 carbon atoms, or a derivative thereof.

2. The radiation-sensitive resin composition according to claim 1, wherein L in formula (1) is 0.

3. The radiation-sensitive resin composition according to claim 1, further comprising a solvent comprising γ-butyrolactone.

4. A radiation-sensitive resin composition comprising:
a salt shown by a following formula (2),

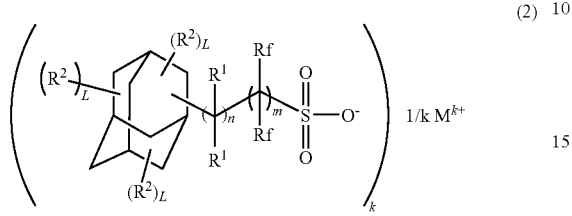

(2)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents 1, m represents 1, $M^{k+}$ represents a k-valent cation, and k represents an integer from 1 to 4; and an acid-dissociable group-containing resin, wherein the resin comprises at least:

a resin that is insoluble or scarcely soluble in alkali and includes a repeating unit (10) shown by the following general formula (10) and a repeating unit obtained by protecting the phenolic hydroxyl group of repeating unit (10) with the acid-dissociable group

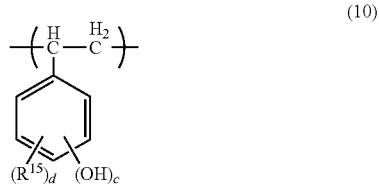

(10)

wherein $R^{15}$ represents a hydrogen atom or a monovalent organic group, and c and d represent an integer from 1 to 3; or (b) a resin that is insoluble or scarcely soluble in alkali and includes a repeating unit shown by the following general formula (13),

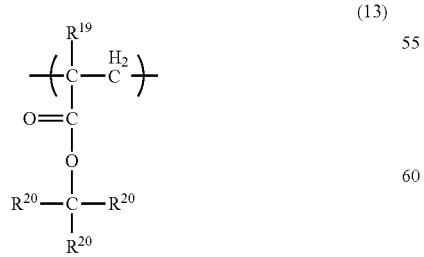

(13)

wherein $R^{19}$ represents a hydrogen atom or a methyl group, and $R^{20}$ represents a monovalent alicyclic hydrocarbon group having 4 to 20 carbon atoms, a derivative thereof, or a linear or branched alkyl group having 1 to 4 carbon atoms, provided that at least one $R^{20}$ is the alicyclic hydrocarbon group or a derivative thereof, or two $R^{20}$ bond to form a divalent alicyclic hydrocarbon group having 4 to 20 carbon atoms or a derivative thereof together with the carbon atom that is bonded to the two $R^{20}$, and the remaining $R^{20}$ is a linear or branched alkyl group having 1 to 4 carbon atoms, a monovalent alicyclic hydrocarbon group having 4 to 20 carbon atoms, or a derivative thereof.

5. The radiation-sensitive resin composition according to claim 4, wherein the k-valent cation in the salt comprises at least one of a sulfonium cation and iodonium cation.

6. The radiation-sensitive resin composition according to claim 4, wherein L in formula (2) is 0.

7. The radiation-sensitive resin composition according to claim 4, further comprising a solvent comprising γ-butyrolactone.

8. A radiation-sensitive resin composition comprising:
a compound shown by a following formula (3),

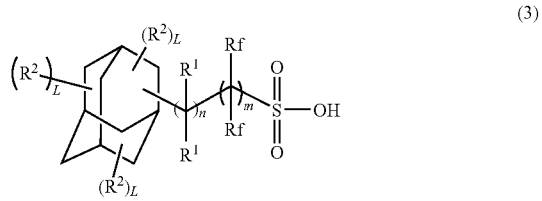

(3)

wherein $R^1$ represents a hydrogen atom or a substituted or unsubstituted hydrocarbon group having 1 to 8 carbon atoms, $R^2$ represents a substituted or unsubstituted hydrocarbon group having 1 to 8 carbon atoms, Rf represents a fluorine atom or a perfluoroalkyl group having 1 to 4 carbon atoms, L represents an integer from 0 to 4, n represents 1, and m represents 1; and an acid-dissociable group-containing resin, wherein the resin comprises at least:

(a) a resin that is insoluble or scarcely soluble in alkali and includes a repeating unit (10) shown by the following general formula (10) and a repeating unit obtained by protecting the phenolic hydroxyl group of repeating unit (10) with the acid-dissociable group

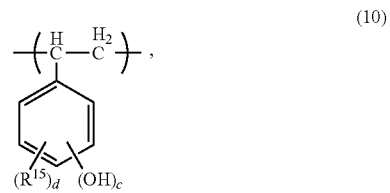

(10)

wherein $R^{15}$ represents a hydrogen atom or a monovalent organic group, and c and d represent an integer from 1 to 3; or (b) a resin that is insoluble or scarcely soluble in alkali and includes a repeating unit shown by the following general formula (13)

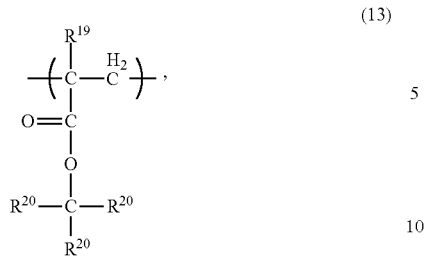
(13)

wherein $R^{19}$ represents a hydrogen atom or a methyl group, and $R^{20}$ represents a monovalent alicyclic hydrocarbon group having 4 to 20 carbon atoms, a derivative thereof, or a linear or branched alkyl group having 1 to 4 carbon atoms, provided that at least one $R^{20}$ is the alicyclic hydrocarbon group or a derivative thereof, or two $R^{20}$ bond to form a divalent alicyclic hydrocarbon group having 4 to 20 carbon atoms or a derivative thereof together with the carbon atom that is bonded to the two $R^{20}$, and the remaining $R^{20}$ is a linear or branched alkyl group having 1 to 4 carbon atoms, a monovalent alicyclic hydrocarbon group having 4 to 20 carbon atoms, or a derivative thereof.

9. The radiation-sensitive resin composition according to claim 8, wherein L in formula (3) is 0.

10. The radiation-sensitive resin composition according to claim 8, further comprising a solvent comprising γ-butyrolactone.

\* \* \* \* \*